(12) United States Patent
Bleck

(10) Patent No.: US 10,137,168 B2
(45) Date of Patent: Nov. 27, 2018

(54) VETERINARY DECORIN COMPOSITIONS AND USE THEREOF

(71) Applicant: CATALENT PHARMA SOLUTIONS, LLC, Somerset, NJ (US)

(72) Inventor: Gregory T. Bleck, Cross Plains, WI (US)

(73) Assignee: CATALENT PHARMA SOLUTIONS, LLC, Somerset, NJ (US)

( * ) Notice: Subject to any disclaimer, the term of this patent is extended or adjusted under 35 U.S.C. 154(b) by 0 days.

(21) Appl. No.: 14/258,197

(22) Filed: Apr. 22, 2014

(65) Prior Publication Data

US 2014/0315806 A1 Oct. 23, 2014

Related U.S. Application Data

(60) Provisional application No. 61/814,405, filed on Apr. 22, 2013.

(51) Int. Cl.
*A61K 38/17* (2006.01)
*C07K 14/47* (2006.01)

(52) U.S. Cl.
CPC ...... *A61K 38/1709* (2013.01); *C07K 14/4725* (2013.01)

(58) Field of Classification Search
CPC .................. A61K 38/1709; C07K 14/4725
See application file for complete search history.

(56) References Cited

U.S. PATENT DOCUMENTS

| | | | |
|---|---|---|---|
| 5,726,149 | A | 3/1998 | Ruoslahti |
| 6,046,162 | A | 4/2000 | Ruoslahti |
| 6,277,812 | B1 | 8/2001 | Ruoslahti |
| 6,436,900 | B1 | 8/2002 | Ruoslahti |
| 6,509,314 | B1 | 1/2003 | Ruoslahti |
| 6,524,573 | B1 | 2/2003 | Iozzo |
| 6,673,341 | B2 | 1/2004 | Sukhatme |
| 2004/0033493 | A1 | 2/2004 | Tchernev |
| 2012/0238727 | A1 | 9/2012 | Bleck et al. |

FOREIGN PATENT DOCUMENTS

| | | |
|---|---|---|
| WO | 1993/009800 | 5/1993 |
| WO | 01/85192 | 11/2001 |
| WO | 2012/125626 | 9/2012 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Laremore et al (Biochem J. Oct. 15, 2010; 431(2): 199-205).*
NCBI Accession P21793 (published Sep. 13, 2005; downloaded from https://www.ncbi.nlm.nih.gov/protein/68845449?sat=34&satkey=4605461 on Sep. 24, 2017). (Year: 2005).*
International Search Report and Written Opinion, International Patent Application No. PCT/US2014/034877, dated Sep. 30, 2014, 15 pages.
Mohan et al. "Decorin transfection suppresses profibrogenic genes and myofibroblast formation in human corneal fibroblasts," Exp Eye Res. 2010, vol. 91, pp. 238-245.
Iozzo et al. "Decorin Antagonizes IGF Receptor I (IGF-IR) Function by interfering with IGF-IR Activity and Attenuating Downstream Signaling," J Biol Chem, 2011, vol. 286, pp. 34712-34721.
Hillier et al., "Sequence and comparative analysis of the chicken genome provide unique perspecitives on vertebrate evolution," Nature, 2004, vol. 432, pp. 695-716.
Examination Report, Australian Patent Application No. 2014257267, dated Mar. 7, 2016.
Donnelly et al. "Decorin-PEI nanoconstruct attenuates equine corneal fibroblast differentiation" Veterinary Ophthalmolgy, vol. 17, No. 3, May 2014, pp. 162-169.
European Search Report, EP Patent Application No. 14788633.7, dated Nov. 8, 2016.
Mohan et al. "Decorin Biology, Expression, Function and Therapy in the Cornea" Current Molecular Medicine, vol. 11, No. 2, 2011, pp. 110-128.
Takanosu M. et al. "Identification of bovine decorin in the fetal bovine rumen." J Vet Med Sci. Feb. 1997;59(2):121-3.

\* cited by examiner

*Primary Examiner* — Brian Gangle
*Assistant Examiner* — Andrea K McCollum
(74) *Attorney, Agent, or Firm* — Casimir Jones S.C.; J. Mitchell Jones

(57) ABSTRACT

The present invention relates to veterinary decorin compositions and methods of their production.

6 Claims, 9 Drawing Sheets

Specification includes a Sequence Listing.

FIG. 3

SEQUENCE LISTING

```
<160> NUMBER OF SEQ ID NOS: 29

<210> SEQ ID NO 1
<211> LENGTH: 1092
<212> TYPE: DNA
<213> ORGANISM: Artificial sequence
<220> FEATURE:
<223> OTHER INFORMATION: Synthetic

<400> SEQUENCE: 1
atgatgtcct ttgtctctct gctcctggta ggcatcctat tccatgccac ccaggccgga      60
ccatttcaac agaaaggctt atttgacttt atgctggaag atgaggctgc agggataggc     120
ccggaagagc actttcctga agttcctgaa atagagccta tgggcccagt ctgccccttc     180
```

-continued

```
cgctgtcagt gccatctgcg agttgtccag tgttctgatc tgggtctgga aaaagtacca      240
aaagaccttc ctcctgatac tgcgctgctg gacctgcaaa acaacaaaat aactgagatc      300
aaagatggag actttaagaa cctgaagaac cttcatacac tgattctcat caacaacaaa      360
attagcaaaa tcagccctgg ggcatttgct cctttggtga aattggaacg actttatctt      420
tccaagaatc aactgaagga attgccagag aaaatgccca aaactcttca ggagctgcgt      480
gtccatgaga acgagatcac caaagtgcga agtctgtgt tcaatggatt gaaccagatg       540
atcgtcgtag aacttggcac caacccgctg aagagctcag gcattgaaaa tggagccttt      600
cagggaatga agaagctctc ctacatccgc attgctgaca caaatataac taccatccct      660
caaggtcttc ctccttccct tactgaatta catctcgatg caacaaaat caccaaagtt       720 gatgcagcta gcctgaaagg actgaataat ttggctaagt tgggactgag tttcaacagc      780
atctctgcgg ttgacaatgg ctctttggcc aacactcctc atttgaggga acttcatttg      840
aacaacaaca agcttgtcaa agtgcccggt gggctggccg atcataagta catccaggtt      900
gtctaccttc acaacaacaa tatctctgca atcggctcta acgacttctg cccacccgga      960
tacaacacca aaaaggcttc ttattcagga gtgagccttt tcagcaaccc agtccagtac     1020
tgggagatcc agccatccac cttccgatgt gtctatgtgc gtgctgccgt tcagcttgga     1080
aactacaagt ga                                                         1092
```

<210> SEQ ID NO 2
<211> LENGTH: 1083
<212> TYPE: DNA
<213> ORGANISM: Artificial sequence
<220> FEATURE:
<223> OTHER INFORMATION: Synthetic

<400> SEQUENCE: 2

```
atgatgtcct ttgtctctct gctcctggta ggcatcctat tccatgccac ccaggccacg       60
cggttccacc agaagggcct cttttgactttt atgatagagg atgaaggggc agccgacatg     120
gctccaacag atgatcctgt catatctgga tttgggccag tgtgcccctt ccgctgccag      180
tgtcatcttc gcgttgtgca gtgctctgac ctaggtctgg aaagagtgcc aaaagacctt      240
ccccctgaca caactctgct ggatttacag aacaacaaaa tcactgaaat taagaagga       300 gatttcaaga atttgaagaa tcttcatgca ttgatccttg ttaacaacaa atcagcaaa       360 ataagtccgg cagcttttgc tcctctgaag aaactggaaa gactgtacct atccaagaat      420
aatttgaagg aacttccaga aaacatgcca agtctcttc aggagatacg tgctcatgaa       480
aatgagatct ccaagttgag gaaggcagtt tttaatggac tgaatcaagt gattgtctta      540
gaactaggca ccaatccact caagagctca ggcattgaaa atggagcttt caagggatg       600 aagaggcttt cctatatccg catcgcagac accaacatta ctagcatccc taaaggtctt      660
cctccatccc ttactgagct tcaccttgat ggcaacaaaa ttagcaaaat tgatgcggaa      720
ggtctgtctg gactcaccaa cttggctaaa ttgggtctca gcttcaacag tatttcttct     780
gttgaaaatg gctctctgaa caatgtacct catctgagag aacttcatct gaataacaac     840
gaacttgtca gagtacctag tgggttgggt gaacacaaat acatccaggt ggtctatctt      900
cataacaaca agattgcttc aattggtatc aacgactttt gccctcttgg ctacaacacc      960
aaaaaggcaa cctattctgg tgtgagtctc ttcagcaacc ccgtgcagta ctgggaaatc     1020 cagcccctctg ctttccgatg tatccatgaa cgctctgcag tacagatcgg aaattacaaa     1080
``` tga                                                                                    1083

<210> SEQ ID NO 3
<211> LENGTH: 360
<212> TYPE: PRT
<213> ORGANISM: Artificial sequence
<220> FEATURE:
<223> OTHER INFORMATION: Synthetic

<400> SEQUENCE: 3

Met Met Ser Phe Val Ser Leu Leu Val Gly Ile Leu Phe His Ala
1               5                   10                  15

Thr Gln Ala Thr Arg Phe His Gln Lys Gly Leu Phe Asp Phe Met Ile
            20                  25                  30

Glu Asp Glu Gly Ala Ala Asp Met Ala Pro Thr Asp Asp Pro Val Ile
        35                  40                  45

Ser Gly Phe Gly Pro Val Cys Pro Phe Arg Cys Gln Cys His Leu Arg
    50                  55                  60

Val Val Gln Cys Ser Asp Leu Gly Leu Glu Arg Val Pro Lys Asp Leu
65                  70                  75                  80

Pro Pro Asp Thr Thr Leu Leu Asp Leu Gln Asn Asn Lys Ile Thr Glu
                85                  90                  95

Ile Lys Glu Gly Asp Phe Lys Asn Leu Lys Asn Leu His Ala Leu Ile
            100                 105                 110

Leu Val Asn Asn Lys Ile Ser Lys Ile Ser Pro Ala Ala Phe Ala Pro
        115                 120                 125

Leu Lys Lys Leu Glu Arg Leu Tyr Leu Ser Lys Asn Asn Leu Lys Glu
    130                 135                 140

Leu Pro Glu Asn Met Pro Lys Ser Leu Gln Glu Ile Arg Ala His Glu
145                 150                 155                 160

Asn Glu Ile Ser Lys Leu Arg Lys Ala Val Phe Asn Gly Leu Asn Gln
                165                 170                 175

Val Ile Val Leu Glu Leu Gly Thr Asn Pro Leu Lys Ser Ser Gly Ile
            180                 185                 190

Glu Asn Gly Ala Phe Gln Gly Met Lys Arg Leu Ser Tyr Ile Arg Ile
        195                 200                 205

Ala Asp Thr Asn Ile Thr Ser Ile Pro Lys Gly Leu Pro Pro Ser Leu
    210                 215                 220

Thr Glu Leu His Leu Asp Gly Asn Lys Ile Ser Lys Ile Asp Ala Glu
225                 230                 235                 240

Gly Leu Ser Gly Leu Thr Asn Leu Ala Lys Leu Gly Leu Ser Phe Asn
                245                 250                 255

Ser Ile Ser Ser Val Glu Asn Gly Ser Leu Asn Asn Val Pro His Leu
            260                 265                 270

Arg Glu Leu His Leu Asn Asn Asn Glu Leu Val Arg Val Pro Ser Gly
        275                 280                 285

Leu Gly Glu His Lys Tyr Ile Gln Val Val Tyr Leu His Asn Asn Lys
    290                 295                 300

Ile Ala Ser Ile Gly Ile Asn Asp Phe Cys Pro Leu Gly Tyr Asn Thr
305                 310                 315                 320

Lys Lys Ala Thr Tyr Ser Gly Val Ser Leu Phe Ser Asn Pro Val Gln
                325                 330                 335

Tyr Trp Glu Ile Gln Pro Ser Ala Phe Arg Cys Ile His Glu Arg Ser
            340                 345                 350

Ala Val Gln Ile Gly Asn Tyr Lys 355                 360

<210> SEQ ID NO 4
<211> LENGTH: 327
<212> TYPE: PRT
<213> ORGANISM: Artificial sequence
<220> FEATURE:
<223> OTHER INFORMATION: Synthetic

<400> SEQUENCE: 4

Asp Glu Gly Ala Ala Asp Met Ala Pro Thr Asp Pro Val Ile Ser
1               5                   10                  15

Gly Phe Gly Pro Val Cys Pro Phe Arg Cys Gln Cys His Leu Arg Val
                20                  25                  30

Val Gln Cys Ser Asp Leu Gly Leu Glu Arg Val Pro Lys Asp Leu Pro
                35                  40                  45

Pro Asp Thr Thr Leu Leu Asp Leu Gln Asn Asn Lys Ile Thr Glu Ile
        50                  55                  60

Lys Glu Gly Asp Phe Lys Asn Leu Lys Asn Leu His Ala Leu Ile Leu
65                  70                  75                  80

Val Asn Asn Lys Ile Ser Lys Ile Ser Pro Ala Ala Phe Ala Pro Leu
                85                  90                  95

Lys Lys Leu Glu Arg Leu Tyr Leu Ser Lys Asn Asn Leu Lys Glu Leu
                100                 105                 110

Pro Glu Asn Met Pro Lys Ser Leu Gln Glu Ile Arg Ala His Glu Asn
                115                 120                 125

Glu Ile Ser Lys Leu Arg Lys Ala Val Phe Asn Gly Leu Asn Gln Val
130                 135                 140

Ile Val Leu Glu Leu Gly Thr Asn Pro Leu Lys Ser Ser Gly Ile Glu
145                 150                 155                 160

Asn Gly Ala Phe Gln Gly Met Lys Arg Leu Ser Tyr Ile Arg Ile Ala
                165                 170                 175

Asp Thr Asn Ile Thr Ser Ile Pro Lys Gly Leu Pro Pro Ser Leu Thr
                180                 185                 190

Glu Leu His Leu Asp Gly Asn Lys Ile Ser Lys Ile Asp Ala Glu Gly
                195                 200                 205

Leu Ser Gly Leu Thr Asn Leu Ala Lys Leu Gly Leu Ser Phe Asn Ser
210                 215                 220

Ile Ser Ser Val Glu Asn Gly Ser Leu Asn Asn Val Pro His Leu Arg
225                 230                 235                 240

Glu Leu His Leu Asn Asn Asn Glu Leu Val Arg Val Pro Ser Gly Leu
                245                 250                 255

Gly Glu His Lys Tyr Ile Gln Val Val Tyr Leu His Asn Asn Lys Ile
                260                 265                 270

Ala Ser Ile Gly Ile Asn Asp Phe Cys Pro Leu Gly Tyr Asn Thr Lys
                275                 280                 285

Lys Ala Thr Tyr Ser Gly Val Ser Leu Phe Ser Asn Pro Val Gln Tyr
                290                 295                 300

Trp Glu Ile Gln Pro Ser Ala Phe Arg Cys Ile His Glu Arg Ser Ala
305                 310                 315                 320

Val Gln Ile Gly Asn Tyr Lys
                325

<210> SEQ ID NO 5
<211> LENGTH: 1092
<212> TYPE: DNA

<213> ORGANISM: Artificial sequence
<220> FEATURE:
<223> OTHER INFORMATION: Synthetic

<400> SEQUENCE: 5

```
atgatgtcct tgtctctct gctcctggta ggcatcctat tccatgccac ccaggccgga      60
ccatttcaac agaaaggctt atttgacttt atgctggaag atgaggctgc agggataggc     120
ccggaagagc actttcctga agttcctgaa atagagccta tgggcccagt ctgccccttc     180
cgctgtcagt gccatctgcg agttgtccag tgttctgatc tgggtctgga aaaagtacca     240
aaagaccttc ctcctgatac tgcgctgctg gacctgcaaa acaacaaaat aactgagatc     300
aaagatggag actttaagaa cctgaagaac cttcatacac tgattctcat caacaacaaa     360
attagcaaaa tcagccctgg ggcatttgct cctttggtga aattggaacg actttatctt     420
tccaagaatc aactgaagga attgccagag aaaatgccca aaactcttca ggagctgcgt     480
gtccatgaga acgagatcac caaagtgcga agtctgtgt tcaatggatt gaaccagatg     540
atcgtcgtag aacttggcac caacccgctg aagagctcag gcattgaaaa tggagccttt     600
cagggaatga agaagctctc ctacatccgc attgctgaca caaatataac taccatccct     660
caaggtcttc ctccttccct tactgaatta catctcgatg caacaaaat caccaaagtt     720
gatgcagcta gcctgaaagg actgaataat ttggctaagt tgggactgag tttcaacagc     780
atctctgcgg ttgacaatgg ctctttggcc aacactcctc atttgaggga acttcatttg     840
aacaacaaca agcttgtcaa agtgcccggt gggctggccg atcataagta catccaggtt     900
gtctaccttc acaacaacaa tatctctgca atcggctcta acgacttctg cccacccgga     960
tacaacacca aaaaggcttc ttattcagga gtgagccttt tcagcaaccc agtccagtac    1020
tgggagatcc agccatccac cttccgatgt gtctatgtgc gtgctgccgt tcagcttgga    1080
aactacaagt ga                                                        1092
```

<210> SEQ ID NO 6
<211> LENGTH: 363
<212> TYPE: PRT
<213> ORGANISM: Artificial sequence
<220> FEATURE:
<223> OTHER INFORMATION: Synthetic

<400> SEQUENCE: 6

```
Met Met Ser Phe Val Ser Leu Leu Leu Val Gly Ile Leu Phe His Ala
1               5                   10                  15

Thr Gln Ala Gly Pro Phe Gln Gln Lys Gly Leu Phe Asp Phe Met Leu
            20                  25                  30

Glu Asp Glu Ala Ala Gly Ile Gly Pro Glu Glu His Phe Pro Glu Val
        35                  40                  45

Pro Glu Ile Glu Pro Met Gly Pro Val Cys Pro Phe Arg Cys Gln Cys
    50                  55                  60

His Leu Arg Val Val Gln Cys Ser Asp Leu Gly Leu Glu Lys Val Pro
65                  70                  75                  80

Lys Asp Leu Pro Pro Asp Thr Ala Leu Leu Asp Leu Gln Asn Asn Lys
                85                  90                  95

Ile Thr Glu Ile Lys Asp Gly Asp Phe Lys Asn Leu Lys Asn Leu His
            100                 105                 110

Thr Leu Ile Leu Ile Asn Asn Lys Ile Ser Lys Ile Ser Pro Gly Ala
        115                 120                 125

Phe Ala Pro Leu Val Lys Leu Glu Arg Leu Tyr Leu Ser Lys Asn Gln
```

```
                130             135             140
Leu Lys Glu Leu Pro Glu Lys Met Pro Lys Thr Leu Gln Glu Leu Arg
145                 150                 155                 160

Val His Glu Asn Glu Ile Thr Lys Val Arg Lys Ser Val Phe Asn Gly
                165                 170                 175

Leu Asn Gln Met Ile Val Val Glu Leu Gly Thr Asn Pro Leu Lys Ser
            180                 185                 190

Ser Gly Ile Glu Asn Gly Ala Phe Gln Gly Met Lys Lys Leu Ser Tyr
        195                 200                 205

Ile Arg Ile Ala Asp Thr Asn Ile Thr Thr Ile Pro Gln Gly Leu Pro
    210                 215                 220

Pro Ser Leu Thr Glu Leu His Leu Asp Gly Asn Lys Ile Thr Lys Val
225                 230                 235                 240

Asp Ala Ala Ser Leu Lys Gly Leu Asn Asn Leu Ala Lys Leu Gly Leu
                245                 250                 255

Ser Phe Asn Ser Ile Ser Ala Val Asp Asn Gly Ser Leu Ala Asn Thr
                260                 265                 270

Pro His Leu Arg Glu Leu His Leu Asn Asn Asn Lys Leu Val Lys Val
            275                 280                 285

Pro Gly Gly Leu Ala Asp His Lys Tyr Ile Gln Val Val Tyr Leu His
        290                 295                 300

Asn Asn Asn Ile Ser Ala Ile Gly Ser Asn Asp Phe Cys Pro Pro Gly
305                 310                 315                 320

Tyr Asn Thr Lys Lys Ala Ser Tyr Ser Gly Val Ser Leu Phe Ser Asn
                325                 330                 335

Pro Val Gln Tyr Trp Glu Ile Gln Pro Ser Thr Phe Arg Cys Val Tyr
            340                 345                 350

Val Arg Ala Ala Val Gln Leu Gly Asn Tyr Lys
        355                 360

<210> SEQ ID NO 7
<211> LENGTH: 330
<212> TYPE: PRT
<213> ORGANISM: Artificial sequence
<220> FEATURE:
<223> OTHER INFORMATION: Synthetic

<400> SEQUENCE: 7

Asp Glu Ala Ala Gly Ile Gly Pro Glu Glu His Phe Pro Glu Val Pro
1               5                   10                  15

Glu Ile Glu Pro Met Gly Pro Val Cys Pro Phe Arg Cys Gln Cys His
            20                  25                  30

Leu Arg Val Val Gln Cys Ser Asp Leu Gly Leu Glu Lys Val Pro Lys
        35                  40                  45

Asp Leu Pro Pro Asp Thr Ala Leu Leu Asp Leu Gln Asn Asn Lys Ile
50                  55                  60

Thr Glu Ile Lys Asp Gly Asp Phe Lys Asn Leu Lys Asn Leu His Thr
65                  70                  75                  80

Leu Ile Leu Ile Asn Asn Lys Ile Ser Lys Ile Ser Pro Gly Ala Phe
                85                  90                  95

Ala Pro Leu Val Lys Leu Glu Arg Leu Tyr Leu Ser Lys Asn Gln Leu
            100                 105                 110

Lys Glu Leu Pro Glu Lys Met Pro Lys Thr Leu Gln Glu Leu Arg Val
        115                 120                 125

His Glu Asn Glu Ile Thr Lys Val Arg Lys Ser Val Phe Asn Gly Leu
```

```
            130                 135                 140
Asn Gln Met Ile Val Val Glu Leu Gly Thr Asn Pro Leu Lys Ser Ser
145                 150                 155                 160

Gly Ile Glu Asn Gly Ala Phe Gln Gly Met Lys Lys Leu Ser Tyr Ile
                165                 170                 175

Arg Ile Ala Asp Thr Asn Ile Thr Thr Ile Pro Gln Gly Leu Pro Pro
            180                 185                 190

Ser Leu Thr Glu Leu His Leu Asp Gly Asn Lys Ile Thr Lys Val Asp
        195                 200                 205

Ala Ala Ser Leu Lys Gly Leu Asn Asn Leu Ala Lys Leu Gly Leu Ser
    210                 215                 220

Phe Asn Ser Ile Ser Ala Val Asp Asn Gly Ser Leu Ala Asn Thr Pro
225                 230                 235                 240

His Leu Arg Glu Leu His Leu Asn Asn Lys Leu Val Lys Val Pro
                245                 250                 255

Gly Gly Leu Ala Asp His Lys Tyr Ile Gln Val Val Tyr Leu His Asn
            260                 265                 270

Asn Asn Ile Ser Ala Ile Gly Ser Asn Asp Phe Cys Pro Pro Gly Tyr
        275                 280                 285

Asn Thr Lys Lys Ala Ser Tyr Ser Gly Val Ser Leu Phe Ser Asn Pro
    290                 295                 300

Val Gln Tyr Trp Glu Ile Gln Pro Ser Thr Phe Arg Cys Val Tyr Val
305                 310                 315                 320

Arg Ala Ala Val Gln Leu Gly Asn Tyr Lys
                325                 330

<210> SEQ ID NO 8
<211> LENGTH: 1092
<212> TYPE: DNA
<213> ORGANISM: Artificial sequence
<220> FEATURE:
<223> OTHER INFORMATION: Synthetic

<400> SEQUENCE: 8
atgatgtcct ttgtctctct gctcctggta ggcatcctat tccatgccac ccaggccggg      60
ccgttccaac agagaggctt atttgacttt atgctagaag atgaggctgc agggataggc     120
ccggaggacc gtgcacctga catgcctgac ctcgagcttc tgggacctgt gtgtcccttc     180
cgctgtcagt gccatctccg agtggtccag tgttccgacc tgggtctgga caaagtacca     240
aaagatcttc cccctgacac tacgctgctc gacttgcaaa acaacaaaat caccgaaatc     300
aaagatggag acttcaagaa cctcaagaac ctgcatacct tgattcttgt aaacaacaaa     360
attagcaaaa tcagccctgg agcatttaca cctttgttga attggaacg actttatctg     420 tccaagaatc atctgaagga attgccagaa aaatgccca aaactcttca ggagctgcgt     480
gcccatgaga atgagatcac caaagttcga aaagctgtgt caatggact gaaccagatg     540 atcgtcgtag agctgggcac caatcccctg aagagttcag ggattgaaaa tggagccttc     600
cagggaatga agaagctctc ctatatccgc attgctgata ccaatataac taccatccct     660
caaggtcttc ctccttccct tactgaatta catcttgaag caacaaaat caccaaggtt     720 gatgcatcta gcctgaaagg actgaataat ttggctaagt tgggactgag ttttaacagc     780
atctccgctg ttgacaatgg cactctagcc aacactcctc atctgaggga gcttcacttg     840
gacaacaata agctcatcag agtacccggt gggctggcgg agcataagta catccaggtt     900
gtctaccttc ataacaacaa tatatctgca gtcggatcta atgacttctg cccacctgga     960
```

```
tacaacacca aaaaggcttc ttattcaggt gtgagccttt tcagcaaccc agtgcagtac    1020
tgggagatcc agccatccac cttccggtgt gtctacgtgc gctctgccat ccagcttgga   1080
aattataaat ga                                                       1092
```

<210> SEQ ID NO 9
<211> LENGTH: 363
<212> TYPE: PRT
<213> ORGANISM: Artificial sequence
<220> FEATURE:
<223> OTHER INFORMATION: Synthetic

<400> SEQUENCE: 9

```
Met Met Ser Phe Val Ser Leu Leu Leu Val Gly Ile Leu Phe His Ala
1               5                   10                  15

Thr Gln Ala Gly Pro Phe Gln Gln Arg Gly Leu Phe Asp Phe Met Leu
            20                  25                  30

Glu Asp Glu Ala Ala Gly Ile Gly Pro Glu Asp Arg Ala Pro Asp Met
        35                  40                  45

Pro Asp Leu Glu Leu Leu Gly Pro Val Cys Pro Phe Arg Cys Gln Cys
    50                  55                  60

His Leu Arg Val Val Gln Cys Ser Asp Leu Gly Leu Asp Lys Val Pro
65                  70                  75                  80

Lys Asp Leu Pro Pro Asp Thr Thr Leu Leu Asp Leu Gln Asn Asn Lys
                85                  90                  95

Ile Thr Glu Ile Lys Asp Gly Asp Phe Lys Asn Leu Lys Asn Leu His
            100                 105                 110

Thr Leu Ile Leu Val Asn Asn Lys Ile Ser Lys Ile Ser Pro Gly Ala
        115                 120                 125

Phe Thr Pro Leu Leu Lys Leu Glu Arg Leu Tyr Leu Ser Lys Asn His
    130                 135                 140

Leu Lys Glu Leu Pro Glu Lys Met Pro Lys Thr Leu Gln Glu Leu Arg
145                 150                 155                 160

Ala His Glu Asn Glu Ile Thr Lys Val Arg Lys Ala Val Phe Asn Gly
                165                 170                 175

Leu Asn Gln Met Ile Val Val Glu Leu Gly Thr Asn Pro Leu Lys Ser
            180                 185                 190

Ser Gly Ile Glu Asn Gly Ala Phe Gln Gly Met Lys Lys Leu Ser Tyr
        195                 200                 205

Ile Arg Ile Ala Asp Thr Asn Ile Thr Thr Ile Pro Gln Gly Leu Pro
    210                 215                 220

Pro Ser Leu Thr Glu Leu His Leu Glu Gly Asn Lys Ile Thr Lys Val
225                 230                 235                 240

Asp Ala Ser Ser Leu Lys Gly Leu Asn Asn Leu Ala Lys Leu Gly Leu
                245                 250                 255

Ser Phe Asn Ser Ile Ser Ala Val Asp Asn Gly Thr Leu Ala Asn Thr
            260                 265                 270

Pro His Leu Arg Glu Leu His Leu Asp Asn Asn Lys Leu Ile Arg Val
        275                 280                 285

Pro Gly Gly Leu Ala Glu His Lys Tyr Ile Gln Val Val Tyr Leu His
    290                 295                 300

Asn Asn Asn Ile Ser Ala Val Gly Ser Asn Asp Phe Cys Pro Pro Gly
305                 310                 315                 320

Tyr Asn Thr Lys Lys Ala Ser Tyr Ser Gly Val Ser Leu Phe Ser Asn
                325                 330                 335
```

Pro Val Gln Tyr Trp Glu Ile Gln Pro Ser Thr Phe Arg Cys Val Tyr
         340                 345                 350

Val Arg Ser Ala Ile Gln Leu Gly Asn Tyr Lys
        355                 360

<210> SEQ ID NO 10
<211> LENGTH: 330
<212> TYPE: PRT
<213> ORGANISM: Artificial sequence
<220> FEATURE:
<223> OTHER INFORMATION: Synthetic

<400> SEQUENCE: 10

Asp Glu Ala Ala Gly Ile Gly Pro Glu Asp Arg Ala Pro Asp Met Pro
1               5                   10                  15

Asp Leu Glu Leu Leu Gly Pro Val Cys Pro Phe Arg Cys Gln Cys His
            20                  25                  30

Leu Arg Val Val Gln Cys Ser Asp Leu Gly Leu Asp Lys Val Pro Lys
        35                  40                  45

Asp Leu Pro Pro Asp Thr Thr Leu Leu Asp Leu Gln Asn Asn Lys Ile
50                  55                  60

Thr Glu Ile Lys Asp Gly Asp Phe Lys Asn Leu Lys Asn Leu His Thr
65                  70                  75                  80

Leu Ile Leu Val Asn Asn Lys Ile Ser Lys Ile Ser Pro Gly Ala Phe
                85                  90                  95

Thr Pro Leu Leu Lys Leu Glu Arg Leu Tyr Leu Ser Lys Asn His Leu
            100                 105                 110

Lys Glu Leu Pro Glu Lys Met Pro Lys Thr Leu Gln Glu Leu Arg Ala
        115                 120                 125

His Glu Asn Glu Ile Thr Lys Val Arg Lys Ala Val Phe Asn Gly Leu
    130                 135                 140

Asn Gln Met Ile Val Glu Leu Gly Thr Asn Pro Leu Lys Ser Ser Ser
145                 150                 155                 160

Gly Ile Glu Asn Gly Ala Phe Gln Gly Met Lys Lys Leu Ser Tyr Ile
                165                 170                 175

Arg Ile Ala Asp Thr Asn Ile Thr Thr Ile Pro Gln Gly Leu Pro Pro
            180                 185                 190

Ser Leu Thr Glu Leu His Leu Glu Gly Asn Lys Ile Thr Lys Val Asp
        195                 200                 205

Ala Ser Ser Leu Lys Gly Leu Asn Asn Leu Ala Lys Leu Gly Leu Ser
    210                 215                 220

Phe Asn Ser Ile Ser Ala Val Asp Asn Gly Thr Leu Ala Asn Thr Pro
225                 230                 235                 240

His Leu Arg Glu Leu His Leu Asp Asn Asn Lys Leu Ile Arg Val Pro
                245                 250                 255

Gly Gly Leu Ala Glu His Lys Tyr Ile Gln Val Val Tyr Leu His Asn
            260                 265                 270

Asn Asn Ile Ser Ala Val Gly Ser Asn Asp Phe Cys Pro Pro Gly Tyr
        275                 280                 285

Asn Thr Lys Lys Ala Ser Tyr Ser Gly Val Ser Leu Phe Ser Asn Pro
    290                 295                 300

Val Gln Tyr Trp Glu Ile Gln Pro Ser Thr Phe Arg Cys Val Tyr Val
305                 310                 315                 320

Arg Ser Ala Ile Gln Leu Gly Asn Tyr Lys
                325                 330

<210> SEQ ID NO 11
<211> LENGTH: 1092
<212> TYPE: DNA
<213> ORGANISM: Artificial sequence
<220> FEATURE:
<223> OTHER INFORMATION: Synthetic

<400> SEQUENCE: 11

```
atgatgtcct ttgtctctct gctcctggta ggcatcctat tccatgccac ccaggccgga      60
ccgtttcaac agaaaggctt atttgacttt atgctggaag atgaggctgc agggatagac     120
ccggaagagc gctttcatga agttcctgaa ttagagccta tgggcccagt ctgccccttc     180
cgctgtcagt gccatctgcg agttgtccag tgttctgttc tgggtctgga aaaagtgccc     240
aaagaccttc ctcctgatac cgcgctgctg gacctgcaaa acaacaaaat aactgagatc     300
aaagatggag actttaagaa cctgaagaac cttcatacac tgattctcat caacaacaaa     360
attagcaaaa tcagccctgg ggcatttgct cctctggtga aattggaacg actttatctt     420
tccaagaatc aactgaagga attgccagag aaaatgccca aaactcttca ggagctgcgt     480
gtccatgaga cgagatcac caaagtgcga agtctgtgt tcaatggatt gaaccagatg      540
atcgtcgtag aacttggcac caacccactg aagagctcag gcattgaaaa tggagccttt     600
cagggaatga gaagctctc ctacatccgc attgctgaca ctaatataac taccattcct     660
caaggtcttc ctccttccct tactgaatta catctcgatg caacaaaat caccaaagtt      720
gatgcagcta gcctgaaagg actgaataat ttggctaagt tgggactgag tttcaacagc     780
atctctgctg ttgacaatgg ctctttagcc aacactcctc atttgaggga acttcatttg     840
aacaacaaca agcttgtcaa agtgcccggt gggctggccg accataagta catccaggtt     900
gtctaccttc acaacaacaa tatctctgca atcggctcca cgacttctg cccacccgga      960
tacaacacca aaaaggcttc ttattcagga gtgagccttt tcagcaaccc agtccagtac    1020
tgggagatcc agccatccac cttccgatgt gtctacgtgc gcgctgctgt tcagcttgga    1080
aactacaagt ga                                                        1092
```

<210> SEQ ID NO 12
<211> LENGTH: 363
<212> TYPE: PRT
<213> ORGANISM: Artificial sequence
<220> FEATURE:
<223> OTHER INFORMATION: Synthetic

<400> SEQUENCE: 12

```
Met Met Ser Phe Val Ser Leu Leu Val Gly Ile Leu Phe His Ala
1               5                   10                  15

Thr Gln Ala Gly Pro Phe Gln Gln Lys Gly Leu Phe Asp Phe Met Leu
            20                  25                  30

Glu Asp Glu Ala Ala Gly Ile Gly Pro Glu Glu Arg Phe His Glu Val
        35                  40                  45

Pro Glu Leu Glu Pro Met Gly Pro Val Cys Pro Phe Arg Cys Gln Cys
    50                  55                  60

His Leu Arg Val Val Gln Cys Ser Val Leu Gly Leu Glu Lys Val Pro
65                  70                  75                  80

Lys Asp Leu Pro Pro Asp Thr Ala Leu Leu Asp Leu Gln Asn Asn Lys
                85                  90                  95

Ile Thr Glu Ile Lys Asp Gly Asp Phe Lys Asn Leu Lys Asn Leu His
            100                 105                 110
```

Thr Leu Ile Leu Ile Asn Asn Lys Ile Ser Lys Ile Ser Pro Gly Ala
            115                 120                 125

Phe Ala Pro Leu Val Lys Leu Glu Arg Leu Tyr Leu Ser Lys Asn Gln
130                 135                 140

Leu Lys Glu Leu Pro Glu Lys Met Pro Lys Thr Leu Gln Glu Leu Arg
145                 150                 155                 160

Val His Glu Asn Glu Ile Thr Lys Val Arg Lys Ser Val Phe Asn Gly
                165                 170                 175

Leu Asn Gln Met Ile Val Val Glu Leu Gly Thr Asn Pro Leu Lys Ser
            180                 185                 190

Ser Gly Ile Glu Asn Gly Ala Phe Gln Gly Met Lys Lys Leu Ser Tyr
        195                 200                 205

Ile Arg Ile Ala Asp Thr Asn Ile Thr Thr Ile Pro Gln Gly Leu Pro
    210                 215                 220

Pro Ser Leu Thr Glu Leu His Leu Asp Gly Asn Lys Ile Thr Lys Val
225                 230                 235                 240

Asp Ala Ala Ser Leu Lys Gly Leu Asn Asn Leu Ala Lys Leu Gly Leu
                245                 250                 255

Ser Phe Asn Ser Ile Ser Ala Val Asp Asn Gly Ser Leu Ala Asn Thr
            260                 265                 270

Pro His Leu Arg Glu Leu His Leu Asn Asn Lys Leu Val Lys Val
        275                 280                 285

Pro Gly Gly Leu Ala Asp His Lys Tyr Ile Gln Val Val Tyr Leu His
    290                 295                 300

Asn Asn Asn Ile Ser Ala Ile Gly Ser Asn Asp Phe Cys Pro Pro Gly
305                 310                 315                 320

Tyr Asn Thr Lys Lys Ala Ser Tyr Ser Gly Val Ser Leu Phe Ser Asn
                325                 330                 335

Pro Val Gln Tyr Trp Glu Ile Gln Pro Ser Thr Phe Arg Cys Val Tyr
            340                 345                 350

Val Arg Ala Ala Val Gln Leu Gly Asn Tyr Lys
        355                 360

<210> SEQ ID NO 13
<211> LENGTH: 330
<212> TYPE: PRT
<213> ORGANISM: Artificial sequence
<220> FEATURE:
<223> OTHER INFORMATION: Synthetic

<400> SEQUENCE: 13

Asp Glu Ala Ala Gly Ile Gly Pro Glu Glu Arg Phe His Glu Val Pro
1               5                   10                  15

Glu Leu Glu Pro Met Gly Pro Val Cys Pro Phe Arg Cys Gln Cys His
            20                  25                  30

Leu Arg Val Val Gln Cys Ser Val Leu Gly Leu Glu Lys Val Pro Lys
        35                  40                  45

Asp Leu Pro Pro Asp Thr Ala Leu Leu Asp Leu Gln Asn Asn Lys Ile
    50                  55                  60

Thr Glu Ile Lys Asp Gly Asp Phe Lys Asn Leu Lys Asn Leu His Thr
65                  70                  75                  80

Leu Ile Leu Ile Asn Asn Lys Ile Ser Lys Ile Ser Pro Gly Ala Phe
                85                  90                  95

Ala Pro Leu Val Lys Leu Glu Arg Leu Tyr Leu Ser Lys Asn Gln Leu
            100                 105                 110

Lys Glu Leu Pro Glu Lys Met Pro Lys Thr Leu Gln Glu Leu Arg Val
            115                 120                 125

His Glu Asn Glu Ile Thr Lys Val Arg Lys Ser Val Phe Asn Gly Leu
        130                 135                 140

Asn Gln Met Ile Val Val Glu Leu Gly Thr Asn Pro Leu Lys Ser Ser
145                 150                 155                 160

Gly Ile Glu Asn Gly Ala Phe Gln Gly Met Lys Lys Leu Ser Tyr Ile
                165                 170                 175

Arg Ile Ala Asp Thr Asn Ile Thr Thr Ile Pro Gln Gly Leu Pro Pro
            180                 185                 190

Ser Leu Thr Glu Leu His Leu Asp Gly Asn Lys Ile Thr Lys Val Asp
        195                 200                 205

Ala Ala Ser Leu Lys Gly Leu Asn Asn Leu Ala Lys Leu Gly Leu Ser
    210                 215                 220

Phe Asn Ser Ile Ser Ala Val Asp Asn Gly Ser Leu Ala Asn Thr Pro
225                 230                 235                 240

His Leu Arg Glu Leu His Leu Asn Asn Asn Lys Leu Val Lys Val Pro
                245                 250                 255

Gly Gly Leu Ala Asp His Lys Tyr Ile Gln Val Val Tyr Leu His Asn
            260                 265                 270

Asn Asn Ile Ser Ala Ile Gly Ser Asn Asp Phe Cys Pro Pro Gly Tyr
        275                 280                 285

Asn Thr Lys Lys Ala Ser Tyr Ser Gly Val Ser Leu Phe Ser Asn Pro
    290                 295                 300

Val Gln Tyr Trp Glu Ile Gln Pro Ser Thr Phe Arg Cys Val Tyr Val
305                 310                 315                 320

Arg Ala Ala Val Gln Leu Gly Asn Tyr Lys
                325                 330

<210> SEQ ID NO 14
<211> LENGTH: 1092
<212> TYPE: DNA
<213> ORGANISM: Artificial sequence
<220> FEATURE:
<223> OTHER INFORMATION: Synthetic

<400> SEQUENCE: 14
atgatgtcct ttgtctctct gctcctggta ggcatcctat tccatgccac ccaggccgga      60
ccatttcaac agagaggctt atttgacttc atgctagaag atgaggctgc agggattggc     120
ccagaagatc gcattcatga agttctagac ttagagcctc tgggaccagt gtgtcctttc     180
cgctgtcagt gccatcttcg agttgtccaa tgttctgatt tgggtctgga caaagtgccc     240
aaagatcttc cccctgacac cacgctgctg gacctgcaaa acaacaaaat aaccgaaatc     300
aaagatggag actttaagaa cctgaagaat cttcatgcgt tgattcttgt caacaacaaa     360
attagcaaaa tcagccctgg agcatttaca cctttggtga actggaacg actttatctg     420 tccaagaatc atttgaagga attgccagaa aaatgccca aaactcttca ggagctgcgt     480
gtccatgaga acgagatcac caaagtgcga aaagcggtgt tcaatggact gaaccagatg     540
atagtcgtag aactgggcac caacccactg aagagctcag gaattgaaaa tggagccttc     600
caggggatga agaagctgtc ctacatccgc attgctgaca ccaacataac caccatccct     660
ccaggtcttc ctccttccct tactgaatta catcttgatg caacaaaat accaaagtt     720 gatgcagcta gcctgagagg actgaataat ttggctaaat tgggactgag tttcaacagc     780

```
atctctgctg ttgacaatgg ctctctggcc aacactcctc atttgaggga acttcacttg    840
gacaacaaca agcttatcaa agtgcctggt gggctggcgg atcataagta catccaggtt    900
gtctaccttc ataacaacaa tatctctgca gttggatcta atgacttctg cccacctgga    960
tacaacacca aaaaggcttc ttattcgggt gtgagccttt tcagcaaccc agtccagtac   1020
tgggagatcc agccatccac cttccgatgt gtctatgtgc gctctgccat tcagctcgga   1080
aactacaagt ga                                                       1092
```

<210> SEQ ID NO 15
<211> LENGTH: 363
<212> TYPE: PRT
<213> ORGANISM: Artificial sequence
<220> FEATURE:
<223> OTHER INFORMATION: Synthetic

<400> SEQUENCE: 15

```
Met Met Ser Phe Val Ser Leu Leu Val Gly Ile Leu Phe His Ala
1               5                   10                  15

Thr Gln Ala Gly Pro Phe Gln Gln Arg Gly Leu Phe Asp Phe Met Leu
            20                  25                  30

Glu Asp Glu Ala Ala Gly Ile Gly Pro Glu Asp Arg Ile His Glu Val
                35                  40                  45

Leu Asp Leu Glu Pro Leu Gly Pro Val Cys Pro Phe Arg Cys Gln Cys
50                  55                  60

His Leu Arg Val Val Gln Cys Ser Asp Leu Gly Leu Asp Lys Val Pro
65                  70                  75                  80

Lys Asp Leu Pro Pro Asp Thr Thr Leu Leu Asp Leu Gln Asn Asn Lys
                85                  90                  95

Ile Thr Glu Ile Lys Asp Gly Asp Phe Lys Asn Leu Lys Asn Leu His
            100                 105                 110

Ala Leu Ile Leu Val Asn Asn Lys Ile Ser Lys Ile Ser Pro Gly Ala
        115                 120                 125

Phe Thr Pro Leu Val Lys Leu Glu Arg Leu Tyr Leu Ser Lys Asn His
    130                 135                 140

Leu Lys Glu Leu Pro Glu Lys Met Pro Lys Thr Leu Gln Glu Leu Arg
145                 150                 155                 160

Val His Glu Asn Glu Ile Thr Lys Val Arg Lys Ala Val Phe Asn Gly
                165                 170                 175

Leu Asn Gln Met Ile Val Val Glu Leu Gly Thr Asn Pro Leu Lys Ser
            180                 185                 190

Ser Gly Ile Glu Asn Gly Ala Phe Gln Gly Met Lys Lys Leu Ser Tyr
        195                 200                 205

Ile Arg Ile Ala Asp Thr Asn Ile Thr Thr Ile Pro Pro Gly Leu Pro
    210                 215                 220

Pro Ser Leu Thr Glu Leu His Leu Asp Gly Asn Lys Ile Thr Lys Val
225                 230                 235                 240

Asp Ala Ala Ser Leu Arg Gly Leu Asn Asn Leu Ala Lys Leu Gly Leu
                245                 250                 255

Ser Phe Asn Ser Ile Ser Ala Val Asp Asn Gly Ser Leu Ala Asn Thr
            260                 265                 270

Pro His Leu Arg Glu Leu His Leu Asp Asn Asn Lys Leu Ile Lys Val
        275                 280                 285

Pro Gly Gly Leu Ala Asp His Lys Tyr Ile Gln Val Val Tyr Leu His
    290                 295                 300
```

```
Asn Asn Asn Ile Ser Ala Val Gly Ser Asn Asp Phe Cys Pro Pro Gly
305                 310                 315                 320

Tyr Asn Thr Lys Lys Ala Ser Tyr Ser Gly Val Ser Leu Phe Ser Asn
            325                 330                 335

Pro Val Gln Tyr Trp Glu Ile Gln Pro Ser Thr Phe Arg Cys Val Tyr
        340                 345                 350

Val Arg Ser Ala Ile Gln Leu Gly Asn Tyr Lys
        355                 360
```

<210> SEQ ID NO 16
<211> LENGTH: 330
<212> TYPE: PRT
<213> ORGANISM: Artificial sequence
<220> FEATURE:
<223> OTHER INFORMATION: Synthetic

<400> SEQUENCE: 16

```
Asp Glu Ala Ala Gly Ile Gly Pro Glu Asp Arg Ile His Glu Val Leu
1               5                   10                  15

Asp Leu Glu Pro Leu Gly Pro Val Cys Pro Phe Arg Cys Gln Cys His
            20                  25                  30

Leu Arg Val Val Gln Cys Ser Asp Leu Gly Leu Asp Lys Val Pro Lys
        35                  40                  45

Asp Leu Pro Pro Asp Thr Thr Leu Leu Asp Leu Gln Asn Asn Lys Ile
50                  55                  60

Thr Glu Ile Lys Asp Gly Asp Phe Lys Asn Leu Lys Asn Leu His Ala
65                  70                  75                  80

Leu Ile Leu Val Asn Asn Lys Ile Ser Lys Ile Ser Pro Gly Ala Phe
                85                  90                  95

Thr Pro Leu Val Lys Leu Glu Arg Leu Tyr Leu Ser Lys Asn His Leu
            100                 105                 110

Lys Glu Leu Pro Glu Lys Met Pro Lys Thr Leu Gln Glu Leu Arg Val
        115                 120                 125

His Glu Asn Glu Ile Thr Lys Val Arg Lys Ala Val Phe Asn Gly Leu
130                 135                 140

Asn Gln Met Ile Val Glu Leu Gly Thr Asn Pro Leu Lys Ser Ser
145                 150                 155                 160

Gly Ile Glu Asn Gly Ala Phe Gln Gly Met Lys Lys Leu Ser Tyr Ile
                165                 170                 175

Arg Ile Ala Asp Thr Asn Ile Thr Thr Ile Pro Pro Gly Leu Pro Pro
            180                 185                 190

Ser Leu Thr Glu Leu His Leu Asp Gly Asn Lys Ile Thr Lys Val Asp
        195                 200                 205

Ala Ala Ser Leu Arg Gly Leu Asn Asn Leu Ala Lys Leu Gly Leu Ser
210                 215                 220

Phe Asn Ser Ile Ser Ala Val Asp Asn Gly Ser Leu Ala Asn Thr Pro
225                 230                 235                 240

His Leu Arg Glu Leu His Leu Asp Asn Asn Lys Leu Ile Lys Val Pro
                245                 250                 255

Gly Gly Leu Ala Asp His Lys Tyr Ile Gln Val Val Tyr Leu His Asn
            260                 265                 270

Asn Asn Ile Ser Ala Val Gly Ser Asn Asp Phe Cys Pro Pro Gly Tyr
        275                 280                 285

Asn Thr Lys Lys Ala Ser Tyr Ser Gly Val Ser Leu Phe Ser Asn Pro
290                 295                 300
```

Val Gln Tyr Trp Glu Ile Gln Pro Ser Thr Phe Arg Cys Val Tyr Val
305                 310                 315                 320

Arg Ser Ala Ile Gln Leu Gly Asn Tyr Lys
                325                 330

<210> SEQ ID NO 17
<211> LENGTH: 1092
<212> TYPE: DNA
<213> ORGANISM: Artificial sequence
<220> FEATURE:
<223> OTHER INFORMATION: Synthetic

<400> SEQUENCE: 17

```
atgatgtcct ttgtctctct gctcctggta ggcatcctat tccatgccac ccaggccgga      60
ccatttcaac agaaaggctt atttgacttt atgctagaag atgaggctgc agggataggc     120
ccagaagacc gctttcctga agttcctgaa ttagagcctc tgggacccat gtgtcccttc     180
cgctgtcaat gccatcttcg agttgtccaa tgttctgatt tgggtctgga caaagtgccc     240
aaagatcttc cacctgacac tgccctgctg atctgcaaa caacaaaat aactgaaatc      300
aaagatggag actttaagaa cctgaagaac cttcatacac tgattctcat caacaacaaa     360
attagcaaaa tcagccctgg agcatttgca cctttggtga attggaacg actttatcta     420
tccaagaatc aactgaagga attgccagag aaaatgccca aaactcttca ggagctgcgt     480
gtccatgaga atgagatcac caaagtgcga aaggctgtgt caatggatt gaaccagatg     540
atcgtcgtag aacttggcac caacccgctg aagagctcag gcattgaaaa cggagctttc     600
cagggaatga agaagctctc ctacatccgc atcgctgaca ccaacattac caccatccct     660
caaggtcttc ctccttccct tactgaatta catcttgatg caacaaaat cagcaaagtt     720
gatgcagcta gcctaaaagg actgaataat ttggctaagt tgggactggg tttcaatagc     780
atctcaactg ttgacaatgg ctctctggcc aacactcctc atttgaggga acttcatctg     840
aacaacaaca agcttaacaa agtgcctggt gggctggcag agcataagta catccaggtt     900
gtctaccttc ataacaacaa catctctgca gtcggctcta atgacttctg cccgcctgga     960
tacaacacca aaaaggcttc ttattcgggg gtgagccttt tcagcaaccc agtccagtac    1020
tgggagatcc agccatccac cttccgatgt gtctatgtgc gctctgccat tcagctcgga    1080
aactacaagt ga                                                        1092
```

<210> SEQ ID NO 18
<211> LENGTH: 363
<212> TYPE: PRT
<213> ORGANISM: Artificial sequence
<220> FEATURE:
<223> OTHER INFORMATION: Synthetic

<400> SEQUENCE: 18

Met Met Ser Phe Val Ser Leu Leu Leu Val Gly Ile Leu Phe His Ala
1               5                   10                  15

Thr Gln Ala Gly Pro Phe Gln Gln Lys Gly Leu Phe Asp Phe Met Leu
            20                  25                  30

Glu Asp Glu Ala Ala Gly Ile Gly Pro Glu Asp Arg Phe Pro Glu Val
        35                  40                  45

Pro Glu Leu Glu Pro Leu Gly Pro Met Cys Pro Phe Arg Cys Gln Cys
    50                  55                  60

His Leu Arg Val Val Gln Cys Ser Asp Leu Gly Leu Asp Lys Val Pro
65                  70                  75                  80

```
Lys Asp Leu Pro Pro Asp Thr Ala Leu Leu Asp Leu Gln Asn Asn Lys
                85                  90                  95

Ile Thr Glu Ile Lys Asp Gly Asp Phe Lys Asn Leu Lys Asn Leu His
            100                 105                 110

Thr Leu Ile Leu Ile Asn Asn Lys Ile Ser Lys Ile Ser Pro Gly Ala
        115                 120                 125

Phe Ala Pro Leu Val Lys Leu Glu Arg Leu Tyr Leu Ser Lys Asn Gln
    130                 135                 140

Leu Lys Glu Leu Pro Glu Lys Met Pro Lys Thr Leu Gln Glu Leu Arg
145                 150                 155                 160

Val His Glu Asn Glu Ile Thr Lys Val Arg Lys Ala Val Phe Asn Gly
                165                 170                 175

Leu Asn Gln Met Ile Val Val Glu Leu Gly Thr Asn Pro Leu Lys Ser
            180                 185                 190

Ser Gly Ile Glu Asn Gly Ala Phe Gln Gly Met Lys Lys Leu Ser Tyr
        195                 200                 205

Ile Arg Ile Ala Asp Thr Asn Ile Thr Thr Ile Pro Gln Gly Leu Pro
    210                 215                 220

Pro Ser Leu Thr Glu Leu His Leu Asp Gly Asn Lys Ile Ser Lys Val
225                 230                 235                 240

Asp Ala Ala Ser Leu Lys Gly Leu Asn Asn Leu Ala Lys Leu Gly Leu
                245                 250                 255

Gly Phe Asn Ser Ile Ser Thr Val Asp Asn Gly Ser Leu Ala Asn Thr
            260                 265                 270

Pro His Leu Arg Glu Leu His Leu Asn Asn Asn Lys Leu Asn Lys Val
        275                 280                 285

Pro Gly Gly Leu Ala Glu His Lys Tyr Ile Gln Val Val Tyr Leu His
    290                 295                 300

Asn Asn Asn Ile Ser Ala Val Gly Ser Asn Asp Phe Cys Pro Pro Gly
305                 310                 315                 320

Tyr Asn Thr Lys Lys Ala Ser Tyr Ser Gly Val Ser Leu Phe Ser Asn
                325                 330                 335

Pro Val Gln Tyr Trp Glu Ile Gln Pro Ser Thr Phe Arg Cys Val Tyr
            340                 345                 350

Val Arg Ser Ala Ile Gln Leu Gly Asn Tyr Lys
        355                 360

<210> SEQ ID NO 19
<211> LENGTH: 330
<212> TYPE: PRT
<213> ORGANISM: Artificial sequence
<220> FEATURE:
<223> OTHER INFORMATION: Synthetic

<400> SEQUENCE: 19

Asp Glu Ala Ala Gly Ile Gly Pro Glu Asp Arg Phe Pro Glu Val Pro
1               5                   10                  15

Glu Leu Glu Pro Leu Gly Pro Met Cys Pro Phe Arg Cys Gln Cys His
            20                  25                  30

Leu Arg Val Val Gln Cys Ser Asp Leu Gly Leu Asp Lys Val Pro Lys
        35                  40                  45

Asp Leu Pro Pro Asp Thr Ala Leu Leu Asp Leu Gln Asn Asn Lys Ile
    50                  55                  60

Thr Glu Ile Lys Asp Gly Asp Phe Lys Asn Leu Lys Asn Leu His Thr
65                  70                  75                  80
```

```
Leu Ile Leu Ile Asn Asn Lys Ile Ser Lys Ile Ser Pro Gly Ala Phe
                85                  90                  95

Ala Pro Leu Val Lys Leu Glu Arg Leu Tyr Leu Ser Lys Asn Gln Leu
            100                 105                 110

Lys Glu Leu Pro Glu Lys Met Pro Lys Thr Leu Gln Glu Leu Arg Val
        115                 120                 125

His Glu Asn Glu Ile Thr Lys Val Arg Lys Ala Val Phe Asn Gly Leu
    130                 135                 140

Asn Gln Met Ile Val Val Glu Leu Gly Thr Asn Pro Leu Lys Ser Ser
145                 150                 155                 160

Gly Ile Glu Asn Gly Ala Phe Gln Gly Met Lys Lys Leu Ser Tyr Ile
                165                 170                 175

Arg Ile Ala Asp Thr Asn Ile Thr Thr Ile Pro Gln Gly Leu Pro Pro
            180                 185                 190

Ser Leu Thr Glu Leu His Leu Asp Gly Asn Lys Ile Ser Lys Val Asp
        195                 200                 205

Ala Ala Ser Leu Lys Gly Leu Asn Asn Leu Ala Lys Leu Gly Leu Gly
    210                 215                 220

Phe Asn Ser Ile Ser Thr Val Asp Asn Gly Ser Leu Ala Asn Thr Pro
225                 230                 235                 240

His Leu Arg Glu Leu His Leu Asn Asn Asn Lys Leu Asn Lys Val Pro
                245                 250                 255

Gly Gly Leu Ala Glu His Lys Tyr Ile Gln Val Val Tyr Leu His Asn
            260                 265                 270

Asn Asn Ile Ser Ala Val Gly Ser Asn Asp Phe Cys Pro Pro Gly Tyr
        275                 280                 285

Asn Thr Lys Lys Ala Ser Tyr Ser Gly Val Ser Leu Phe Ser Asn Pro
    290                 295                 300

Val Gln Tyr Trp Glu Ile Gln Pro Ser Thr Phe Arg Cys Val Tyr Val
305                 310                 315                 320

Arg Ser Ala Ile Gln Leu Gly Asn Tyr Lys
                325                 330

<210> SEQ ID NO 20
<211> LENGTH: 1092
<212> TYPE: DNA
<213> ORGANISM: Artificial sequence
<220> FEATURE:
<223> OTHER INFORMATION: Synthetic

<400> SEQUENCE: 20
atgatgtcct ttgtctctct gctcctggta ggcatcctat tccatgccac ccaggccgga      60
ccgtttcaac agaaaggctt atttgacttt atgctggaag atgaggctgc agggataggc     120
ccggaagagc gctttcatga ggttcctgaa ttagagccta tgggcccagt ctgccccttc     180
cgttgccagt gccatctgcg agttgtccag tgttctgatc tgggtctgga aaaagtgccc     240
aaagaccttc ctcctgatac cgcgctgctg gacctgcaaa caacaaaat aactgagatc     300 aaagatggag actttaaaaa cctgaagaac cttcatacac tgattctcat caacaacaaa     360
attagcaaaa ttagccctgg ggcatttgct cctctggtga aattggaacg actttatctt     420
tccaagaatc aactgaagga attgccagag aaaatgccca aactcttca ggagctgcgt      480 gtccatgaga acgagatcac caaagtgcga agtctgtgt tcaatggatt gaaccagatg      540
atcgtcgtag aacttggcac caacccactg aagagctcag gcattgaaaa tggagccttt     600
cagggaatga agaagctctc ctacatccgc attgctgaca ctaatataac taccatccct     660
```

```
caaggtcttc ctccttccct tactgaatta catctcgacg gcaacaaaat caccaaagtt    720
gatgcagcta gcctgaaagg actgaataat ttggctaagt tgggactgag tttcaacagc    780
atctctgctg ttgacaatgg ctctttggcc aacactcctc atttgaggga acttcatttg    840
aacaacaaca agcttgtcaa agtgcccggt gggctggccg accataagta catccaggtt    900
gtctaccttc acaacaacaa tatctctgca atcggctcta acgacttctg cccacctgga    960
tacaacacca aaaaggcttc ttattcagga gtgagccttt tcagcaaccc agtccagtac   1020
tgggagatcc agccatccac cttccgatgt gtctacgtgc cgctgctgt tcagcttgga   1080 aactacaagt ga                                                      1092
```

<210> SEQ ID NO 21
<211> LENGTH: 363
<212> TYPE: PRT
<213> ORGANISM: Artificial sequence
<220> FEATURE:
<223> OTHER INFORMATION: Synthetic

<400> SEQUENCE: 21

Met Met Ser Phe Val Ser Leu Leu Val Gly Ile Leu Phe His Ala
1               5                   10                  15

Thr Gln Ala Gly Pro Phe Gln Gln Lys Gly Leu Phe Asp Phe Met Leu
        20                  25                  30

Glu Asp Glu Ala Ala Gly Ile Gly Pro Glu Glu Arg Phe His Glu Val
            35                  40                  45

Pro Glu Leu Glu Pro Met Gly Pro Val Cys Pro Phe Arg Cys Gln Cys
    50                  55                  60

His Leu Arg Val Val Gln Cys Ser Asp Leu Gly Leu Glu Lys Val Pro
65                  70                  75                  80

Lys Asp Leu Pro Pro Asp Thr Ala Leu Leu Asp Leu Gln Asn Asn Lys
                85                  90                  95

Ile Thr Glu Ile Lys Asp Gly Asp Phe Lys Asn Leu Lys Asn Leu His
            100                 105                 110

Thr Leu Ile Leu Ile Asn Asn Lys Ile Ser Lys Ile Ser Pro Gly Ala
        115                 120                 125

Phe Ala Pro Leu Val Lys Leu Glu Arg Leu Tyr Leu Ser Lys Asn Gln
    130                 135                 140

Leu Lys Glu Leu Pro Glu Lys Met Pro Lys Thr Leu Gln Glu Leu Arg
145                 150                 155                 160

Val His Glu Asn Glu Ile Thr Lys Val Arg Lys Ser Val Phe Asn Gly
                165                 170                 175

Leu Asn Gln Met Ile Val Val Glu Leu Gly Thr Asn Pro Leu Lys Ser
            180                 185                 190

Ser Gly Ile Glu Asn Gly Ala Phe Gln Gly Met Lys Lys Leu Ser Tyr
        195                 200                 205

Ile Arg Ile Ala Asp Thr Asn Ile Thr Thr Ile Pro Gln Gly Leu Pro
    210                 215                 220

Pro Ser Leu Thr Glu Leu His Leu Asp Gly Asn Lys Ile Thr Lys Val
225                 230                 235                 240

Asp Ala Ala Ser Leu Lys Gly Leu Asn Asn Leu Ala Lys Leu Gly Leu
                245                 250                 255

Ser Phe Asn Ser Ile Ser Ala Val Asp Asn Gly Ser Leu Ala Asn Thr
            260                 265                 270

Pro His Leu Arg Glu Leu His Leu Asn Asn Asn Lys Leu Val Lys Val

```
                275                 280                 285
Pro Gly Gly Leu Ala Asp His Lys Tyr Ile Gln Val Val Tyr Leu His
    290                 295                 300
Asn Asn Asn Ile Ser Ala Ile Gly Ser Asn Asp Phe Cys Pro Pro Gly
305                 310                 315                 320
Tyr Asn Thr Lys Lys Ala Ser Tyr Ser Gly Val Ser Leu Phe Ser Asn
                325                 330                 335
Pro Val Gln Tyr Trp Glu Ile Gln Pro Ser Thr Phe Arg Cys Val Tyr
                340                 345                 350
Val Arg Ala Ala Val Gln Leu Gly Asn Tyr Lys
                355                 360

<210> SEQ ID NO 22
<211> LENGTH: 330
<212> TYPE: PRT
<213> ORGANISM: Artificial sequence
<220> FEATURE:
<223> OTHER INFORMATION: Synthetic

<400> SEQUENCE: 22

Asp Glu Ala Ala Gly Ile Gly Pro Glu Glu Arg Phe His Glu Val Pro
1               5                   10                  15
Glu Leu Glu Pro Met Gly Pro Val Cys Pro Phe Arg Cys Gln Cys His
                20                  25                  30
Leu Arg Val Val Gln Cys Ser Asp Leu Gly Leu Glu Lys Val Pro Lys
                35                  40                  45
Asp Leu Pro Pro Asp Thr Ala Leu Leu Asp Leu Gln Asn Asn Lys Ile
            50                  55                  60
Thr Glu Ile Lys Asp Gly Asp Phe Lys Asn Leu Lys Asn Leu His Thr
65              70                  75                  80
Leu Ile Leu Ile Asn Asn Lys Ile Ser Lys Ile Ser Pro Gly Ala Phe
                85                  90                  95
Ala Pro Leu Val Lys Leu Glu Arg Leu Tyr Leu Ser Lys Asn Gln Leu
                100                 105                 110
Lys Glu Leu Pro Glu Lys Met Pro Lys Thr Leu Gln Glu Leu Arg Val
                115                 120                 125
His Glu Asn Glu Ile Thr Lys Val Arg Lys Ser Val Phe Asn Gly Leu
            130                 135                 140
Asn Gln Met Ile Val Val Glu Leu Gly Thr Asn Pro Leu Lys Ser Ser
145                 150                 155                 160
Gly Ile Glu Asn Gly Ala Phe Gln Gly Met Lys Lys Leu Ser Tyr Ile
                165                 170                 175
Arg Ile Ala Asp Thr Asn Ile Thr Thr Ile Pro Gln Gly Leu Pro Pro
                180                 185                 190
Ser Leu Thr Glu Leu His Leu Asp Gly Asn Lys Ile Thr Lys Val Asp
                195                 200                 205
Ala Ala Ser Leu Lys Gly Leu Asn Asn Leu Ala Lys Leu Gly Leu Ser
            210                 215                 220
Phe Asn Ser Ile Ser Ala Val Asp Asn Gly Ser Leu Ala Asn Thr Pro
225                 230                 235                 240
His Leu Arg Glu Leu His Leu Asn Asn Asn Lys Leu Val Lys Val Pro
                245                 250                 255
Gly Gly Leu Ala Asp His Lys Tyr Ile Gln Val Val Tyr Leu His Asn
                260                 265                 270
Asn Asn Ile Ser Ala Ile Gly Ser Asn Asp Phe Cys Pro Pro Gly Tyr
```

```
             275                 280                 285
Asn Thr Lys Lys Ala Ser Tyr Ser Gly Val Ser Leu Phe Ser Asn Pro
    290                 295                 300

Val Gln Tyr Trp Glu Ile Gln Pro Ser Thr Phe Arg Cys Val Tyr Val
305                 310                 315                 320

Arg Ala Ala Val Gln Leu Gly Asn Tyr Lys
                325                 330

<210> SEQ ID NO 23
<211> LENGTH: 19
<212> TYPE: PRT
<213> ORGANISM: Artificial sequence
<220> FEATURE:
<223> OTHER INFORMATION: Synthetic

<400> SEQUENCE: 23

Met Met Ser Phe Val Ser Leu Leu Leu Val Gly Ile Leu Phe His Ala
1               5                   10                  15

Thr Gln Ala

<210> SEQ ID NO 24
<211> LENGTH: 57
<212> TYPE: DNA
<213> ORGANISM: Artificial sequence
<220> FEATURE:
<223> OTHER INFORMATION: Synthetic

<400> SEQUENCE: 24
atgatgtcct ttgtctctct gctcctggta ggcatcctat tccatgccac ccaggcc          57

<210> SEQ ID NO 25
<211> LENGTH: 1092
<212> TYPE: DNA
<213> ORGANISM: Artificial sequence
<220> FEATURE:
<223> OTHER INFORMATION: Synthetic

<400> SEQUENCE: 25
atgatgtcct ttgtctctct gctcctggta ggcatcctat tccatgccac ccaggccggg       60
ccgttccaac agagaggctt atttgacttt atgctagaag atgaggctgc agggataggc      120
ccagaagagc acgctcctgt tgattctgat ttagagcctc tggggccagt gtgtccttc       180 cgctgtcagt gccaccttcg agttgtgcag tgttctgatt tgggtttgga aaaagtgcca      240
aaagagctcc ctcctgacac tacgctgctg acttgcaaa caacaaaat aaccgaaatc       300 aaagatggag acttcaagaa cctgaagaac cttcatacgt tgatccttgt caacaacaaa      360
attagcaaaa tcagccctgg agcatttaca cctttgttga attggaacg actttatctg       420 tccaagaatc atctgaagga attgccagaa aaatgccca aaactcttca ggagctgcgt       480
gctcacgaga tgagatcac caaagtgcga aaagctgtgt caatggcct gaaccagatg       540 atcgtcgtag aactgggcac caacccgctg aagagctcgg aattgaaaa tggagccttc       600 cagggaatga agaagctgtc ctacatccgc attgccgaca ccaatataac caccatcccg       660
caaggtcttc ctccttccct tactgaatta catcttgaag caacaaaat ctccaaagtt       720 gatgcagcta gcctgaaagg actgaataat ttggctaagt tgggactgag ttttaacagc      780
atctctgcta ttgacaatgg cactctggcc aacactcctc atttgagga gcttcacttg      840 gacaacaata agcttatcag agtacctggt gggctggcgg agcacaaata catccaggtt      900
gtctaccttc ataacaacaa tatctctgca gtcgggtcta cgacttctg cccacctgga       960
```
tacaacacca aaaaggcttc ttattcaggt gtgagccttt tcagcaaccc agtccagtac    1020
tgggagatcc aaccatccac cttccgatgt gtctatgtgc gttccgccat ccagcttgga    1080
aattataaat ga    1092

<210> SEQ ID NO 26
<211> LENGTH: 363
<212> TYPE: PRT
<213> ORGANISM: Artificial sequence
<220> FEATURE:
<223> OTHER INFORMATION: Synthetic

<400> SEQUENCE: 26

Met Met Ser Phe Val Ser Leu Leu Val Gly Ile Leu Phe His Ala
1               5                   10                  15

Thr Gln Ala Gly Pro Phe Gln Gln Arg Gly Leu Phe Asp Phe Met Leu
            20                  25                  30

Glu Asp Glu Ala Ala Gly Ile Gly Pro Glu Glu His Ala Pro Val Asp
        35                  40                  45

Ser Asp Leu Glu Pro Leu Gly Pro Val Cys Pro Phe Arg Cys Gln Cys
    50                  55                  60

His Leu Arg Val Val Gln Cys Ser Asp Leu Gly Leu Glu Lys Val Pro
65                  70                  75                  80

Lys Glu Leu Pro Pro Asp Thr Thr Leu Leu Asp Leu Gln Asn Asn Lys
                85                  90                  95

Ile Thr Glu Ile Lys Asp Gly Asp Phe Lys Asn Leu Lys Asn Leu His
            100                 105                 110

Thr Leu Ile Leu Val Asn Asn Lys Ile Ser Lys Ile Ser Pro Gly Ala
        115                 120                 125

Phe Thr Pro Leu Leu Lys Leu Glu Arg Leu Tyr Leu Ser Lys Asn His
    130                 135                 140

Leu Lys Glu Leu Pro Glu Lys Met Pro Lys Thr Leu Gln Glu Leu Arg
145                 150                 155                 160

Ala His Glu Asn Glu Ile Thr Lys Val Arg Lys Ala Val Phe Asn Gly
                165                 170                 175

Leu Asn Gln Met Ile Val Val Glu Leu Gly Thr Asn Pro Leu Lys Ser
            180                 185                 190

Ser Gly Ile Glu Asn Gly Ala Phe Gln Gly Met Lys Lys Leu Ser Tyr
        195                 200                 205

Ile Arg Ile Ala Asp Thr Asn Ile Thr Thr Ile Pro Gln Gly Leu Pro
    210                 215                 220

Pro Ser Leu Thr Glu Leu His Leu Glu Gly Asn Lys Ile Ser Lys Val
225                 230                 235                 240

Asp Ala Ala Ser Leu Lys Gly Leu Asn Asn Leu Ala Lys Leu Gly Leu
                245                 250                 255

Ser Phe Asn Ser Ile Ser Ala Ile Asp Asn Gly Thr Leu Ala Asn Thr
            260                 265                 270

Pro His Leu Arg Glu Leu His Leu Asp Asn Asn Lys Leu Ile Arg Val
        275                 280                 285

Pro Gly Gly Leu Ala Glu His Lys Tyr Ile Gln Val Val Tyr Leu His
    290                 295                 300

Asn Asn Asn Ile Ser Ala Val Gly Ser Asn Asp Phe Cys Pro Pro Gly
305                 310                 315                 320

Tyr Asn Thr Lys Lys Ala Ser Tyr Ser Gly Val Ser Leu Phe Ser Asn
                325                 330                 335

-continued

Pro Val Gln Tyr Trp Glu Ile Gln Pro Ser Thr Phe Arg Cys Val Tyr
            340                 345                 350

Val Arg Ser Ala Ile Gln Leu Gly Asn Tyr Lys
            355                 360

<210> SEQ ID NO 27
<211> LENGTH: 330
<212> TYPE: PRT
<213> ORGANISM: Artificial sequence
<220> FEATURE:
<223> OTHER INFORMATION: Synthetic

<400> SEQUENCE: 27

Asp Glu Ala Ala Gly Ile Gly Pro Glu Glu His Ala Pro Val Asp Ser
1               5                   10                  15

Asp Leu Glu Pro Leu Gly Pro Val Cys Pro Phe Arg Cys Gln Cys His
            20                  25                  30

Leu Arg Val Val Gln Cys Ser Asp Leu Gly Leu Glu Lys Val Pro Lys
        35                  40                  45

Glu Leu Pro Pro Asp Thr Thr Leu Leu Asp Leu Gln Asn Asn Lys Ile
    50                  55                  60

Thr Glu Ile Lys Asp Gly Asp Phe Lys Asn Leu Lys Asn Leu His Thr
65                  70                  75                  80

Leu Ile Leu Val Asn Asn Lys Ile Ser Lys Ile Ser Pro Gly Ala Phe
                85                  90                  95

Thr Pro Leu Leu Lys Leu Glu Arg Leu Tyr Leu Ser Lys Asn His Leu
            100                 105                 110

Lys Glu Leu Pro Glu Lys Met Pro Lys Thr Leu Gln Glu Leu Arg Ala
        115                 120                 125

His Glu Asn Glu Ile Thr Lys Val Arg Lys Ala Val Phe Asn Gly Leu
    130                 135                 140

Asn Gln Met Ile Val Glu Leu Gly Thr Asn Pro Leu Lys Ser Ser Gly
145                 150                 155                 160

Gly Ile Glu Asn Gly Ala Phe Gln Gly Met Lys Lys Leu Ser Tyr Ile
                165                 170                 175

Arg Ile Ala Asp Thr Asn Ile Thr Thr Ile Pro Gln Gly Leu Pro Pro
            180                 185                 190

Ser Leu Thr Glu Leu His Leu Glu Gly Asn Lys Ile Ser Lys Val Asp
        195                 200                 205

Ala Ala Ser Leu Lys Gly Leu Asn Asn Leu Ala Lys Leu Gly Leu Ser
    210                 215                 220

Phe Asn Ser Ile Ser Ala Ile Asp Asn Gly Thr Leu Ala Asn Thr Pro
225                 230                 235                 240

His Leu Arg Glu Leu His Leu Asp Asn Asn Lys Leu Ile Arg Val Pro
                245                 250                 255

Gly Gly Leu Ala Glu His Lys Tyr Ile Gln Val Val Tyr Leu His Asn
            260                 265                 270

Asn Asn Ile Ser Ala Val Gly Ser Asn Asp Phe Cys Pro Pro Gly Tyr
        275                 280                 285

Asn Thr Lys Lys Ala Ser Tyr Ser Gly Val Ser Leu Phe Ser Asn Pro
    290                 295                 300

Val Gln Tyr Trp Glu Ile Gln Pro Ser Thr Phe Arg Cys Val Tyr Val
305                 310                 315                 320

Arg Ser Ala Ile Gln Leu Gly Asn Tyr Lys
                325                 330

<210> SEQ ID NO 28
<211> LENGTH: 1119
<212> TYPE: DNA
<213> ORGANISM: Artificial sequence
<220> FEATURE:
<223> OTHER INFORMATION: Synthetic

<400> SEQUENCE: 28

| | | | | | |
|---|---|---|---|---|---|
| aagcttgccg | ccaccatgat | gtcctttgtc | tctctgctcc | tggtaggcat | cctattccat | 60 |
| gccacccagg | ccgggccgtt | ccaacagaga | ggcttatttg | actttatgct | agaagatgag | 120 |
| gctgcaggga | taggcccgga | ggaccgtgca | cctgacatgc | ctgacctcga | gcttctggga | 180 |
| cctgtgtgtc | ccttccgctg | tcagtgccat | ctccgagtgg | tccagtgttc | cgacctgggt | 240 |
| ctggacaaag | taccaaaaga | tcttcccccct | gacactacgc | tgctcgactt | gcaaaacaac | 300 |
| aaaatcaccg | aaatcaaaga | tggagacttc | aagaacctca | agaacctgca | taccttgatt | 360 |
| cttgtaaaca | acaaaattag | caaaatcagc | cctggagcat | ttacaccttt | gttgaaattg | 420 |
| gaacgacttt | atctgtccaa | gaatcatctg | aaggaattgc | agaaaaaat | gcccaaaact | 480 |
| cttcaggagc | tgcgtgccca | tgagaatgag | atcaccaaag | ttcgaaaagc | tgtgttcaat | 540 |
| ggactgaacc | agatgatcgt | cgtagagctg | ggcaccaatc | ccctgaagag | ttcagggatt | 600 |
| gaaaatggag | ccttccaggg | aatgaagaag | ctctcctata | tccgcattgc | tgataccaat | 660 |
| ataactacca | tccctcaagg | tcttcctcct | tcccttactg | aattacatct | tgaaggcaac | 720 |
| aaaatcacca | aggttgatgc | atctagcctg | aaaggactga | ataatttggc | taagttggga | 780 |
| ctgagttttta | acagcatctc | cgctgttgac | aatggcactc | tagccaacac | tcctcatctg | 840 |
| agggagcttc | acttggacaa | caataagctc | atcagagtac | ccggtgggct | ggcggagcat | 900 |
| aagtacatcc | aggttgtcta | ccttcataac | aacaatatat | ctgcagtcgg | atctaatgac | 960 |
| ttctgcccac | ctggatacaa | caccaaaaag | gcttcttatt | caggtgtgag | cctttttcagc | 1020 |
| aacccagtgc | agtactggga | gatccagcca | tccaccttcc | ggtgtgtcta | cgtgcgctct | 1080 |
| gccatccagc | ttggaaatta | taaatgatga | gatctcgag | | | 1119 |

<210> SEQ ID NO 29
<211> LENGTH: 1119
<212> TYPE: DNA
<213> ORGANISM: Artificial sequence
<220> FEATURE:
<223> OTHER INFORMATION: Synthetic

<400> SEQUENCE: 29

| | | | | | |
|---|---|---|---|---|---|
| aagcttgccg | ccaccatgat | gtcctttgtc | tctctgctcc | tggtaggcat | cctattccat | 60 |
| gccacccagg | ccgggccgtt | ccaacagaga | ggcttatttg | actttatgct | agaagatgag | 120 |
| gctgcaggga | taggcccaga | agagcacgct | cctgttgatt | ctgatttaga | gcctctgggg | 180 |
| ccagtgtgtc | ctttccgctg | tcagtgccac | cttcgagttg | tgcagtgttc | tgatttgggt | 240 |
| ttggaaaaag | tgccaaaaga | gctccctcct | gacactacgc | tgctggactt | gcaaaacaac | 300 |
| aaaataaccg | aaatcaaaga | tggagacttc | aagaacctga | agaacttca | tacgttgatc | 360 |
| cttgtcaaca | acaaaattag | caaaatcagc | cctggagcat | ttacaccttt | gttgaaattg | 420 |
| gaacgacttt | atctgtccaa | gaatcatctg | aaggaattgc | agaaaaaat | gcccaaaact | 480 |
| cttcaggagc | tgcgtgctca | cgagaatgag | atcaccaaag | tgcgaaaagc | tgtgttcaat | 540 |
| ggcctgaacc | agatgatcgt | cgtagaactg | ggcaccaacc | cgctgaagag | ctcgggaatt | 600 |

```
gaaaatggag ccttccaggg aatgaagaag ctgtcctaca tccgcattgc cgacaccaat    660
ataaccacca tcccgcaagg tcttcctcct tcccttactg aattacatct tgaaggcaac    720
aaaatctcca aagttgatgc agctagcctg aaaggactga ataatttggc taagttggga    780
ctgagtttta acagcatctc tgctattgac aatggcactc tggccaacac tcctcatttg    840
agggagcttc acttggacaa caataagctt atcagagtac ctggtgggct ggcggagcac    900
aaatacatcc aggttgtcta ccttcataac aacaatatct ctgcagtcgg gtctaacgac    960
ttctgcccac ctggatacaa caccaaaaag gcttcttatt caggtgtgag cctttcagc    1020 aacccagtcc agtactggga gatccaacca tccaccttcc gatgtgtcta tgtgcgttcc    1080
gccatccagc ttggaaatta taaatgatga gatctcgag                          1119
```

VETERINARY DECORIN COMPOSITIONS AND USE THEREOF

CROSS-REFERENCE TO RELATED APPLICATIONS

This application claims the benefit of U.S. Prov. Appl. 61/814,405 filed Apr. 22, 2013, the entire contents of which are incorporated herein by reference.

FIELD OF THE INVENTION

The present invention relates to veterinary decorin compositions and methods of their production and use.

BACKGROUND OF THE INVENTION

Proteoglycans carrying one or more glycosaminoglycan (GAG) chains form a large gene family that may be classified into five groups according to the structural properties of the core protein. One of the groups is the small Leucine-rich proteoglycan family comprised of decorin (DCN), biglycan, fibromodulin and lumican. These are characterized by 40 kDa core proteins that contain Leucine-rich repeats of approximately 12 amino acids. DCN is a prototype of the group and is also referred to as PG-S2, PG40, proteodermatan sulphate and DS-PGII. It contains one dermatan chondroitin sulphate GAG chain covalently linked to a Serine of the mature core protein and is considered to be a multifunctional proteoglycan.

Decorin protein is present in most all animal tissues. The reduction or absence of decorin leads to problems within the body. The proposed functions of DCN include, but are not limited to, regulation of collagen fibrillogenesis, maintenance of tissue integrity via binding with fibronectin and thrombospondin, and a reservoir of transforming growth factor β (TGF-β). The latter function of DCN is achieved through its core protein sequestering the growth factor in the extracellular milieu from receptors expressed on the cell surface. Various conditions including all types of surgery, cuts, burns, eye injuries, spinal cord injury, head trauma, lung disease, kidney disease, liver disease and cancer can disrupt the balance of decorin in the effected tissue.

Therapeutic use of decorin in humans has been proposed. Examples of such uses include: suppression of cell proliferation by decorin (U.S. Pat. No. 6,046,162); methods for inhibiting TGF-beta activity (U.S. Pat. No. 6,277,812); methods of a pathology or a fibrotic condition by administering decorin (U.S. Pat. No. 6,436,900); methods of preventing or reducing scarring with decorin or biglycan (U.S. Pat. No. 6,509,314), treatment of glomerulonephritis with decorin (U.S. Pat. No. 5,726,149); suppressing tumor cell growth by administering decorin (U.S. Pat. No. 6,524,573); and inhibiting proliferative diseases by inhibiting TGF-beta mediated angiogenesis (U.S. Pat. No. 6,673,341). All of the patents referenced in this paragraph are incorporated herein by reference in their entirety.

What is needed in the art are decorin compositions for use in veterinary therapies.

SUMMARY OF THE INVENTION

The present invention relates to veterinary decorin compositions and methods of their production and use.

In some embodiments, the present invention provides a veterinary decorin core protein molecule that is at least 95% identical to one of SEQ ID NOs: 4, 7, 10, 13, 16, 19, 22, and 27, with the proviso that the veterinary decorin core protein comprises a mutation at amino acid 4. In some embodiments, the mutation prevents gagylation of the molecule. In some embodiments, the mutation is a serine to alanine mutation. In some embodiments, the protein molecule is at least 98% identical to one of SEQ ID NOs: 4, 7, 10, 13, 16, 19, 22, and 27, with the proviso that the veterinary decorin core protein comprises a mutation at amino acid 4. In some embodiments, the protein molecule is at least 99% identical to one of SEQ ID NOs: 4, 7, 10, 13, 16, 19, 22, and 27, with the proviso that the veterinary decorin core protein comprises a mutation at amino acid 4. In some embodiments, the protein molecule is 100% identical to one of SEQ ID NOs: 4, 7, 10, 13, 16, 19, 22, and 27, with the proviso that the veterinary decorin core protein comprises a mutation at amino acid 4. In some embodiments, the core molecule is operably linked to an exogenous signal peptide. In some embodiments, the exogenous signal peptide is a bovine lactalbumin signal peptide.

In some embodiments, the present invention provides a composition comprising a veterinary decorin core protein molecule according as described above in combination with a pharmaceutically acceptable carrier.

In some embodiments, the present invention provides a nucleic acid sequence encoding a veterinary decorin core molecule as described above. In some embodiments, the nucleic acid sequence encoding a veterinary decorin core molecule is operably associated with an exogenous signal peptide. In some embodiments, the exogenous signal peptide is a bovine lactalbumin signal peptide.

In some embodiments, the present invention provides a host cell comprising the expression vector as described above.

In some embodiments, the present invention provides a method of producing a veterinary decorin protein comprising expressing the expression vector as described above in a host cell to produce the veterinary decorin protein and purifying the veterinary decorin protein.

In some embodiments, the present invention provides a pharmaceutical formulation comprising a veterinary decorin core protein molecule as described above, wherein the formulation is a liquid, powder, spray, gel, ointment, lotion, or eye drop.

In some embodiments, the present invention provides methods of treating a veterinary subject in need thereof comprising administering to the subject a veterinary decorin core protein according to claim 1 in an effective amount. In some embodiments, the veterinary decorin core protein is administered by a method selected from the group consisting of enteral, parenteral and topical administration. In some embodiments, the veterinary decorin core protein is administered by a method selected from the group consisting of oral administration, intravenous administration, intradermal administration, subcutaneous administration, transdermal administration, nasal administration, intramuscular administration, intrathecal administration, intraocular administration, intravitreal administration, intravaginal administration, and transmucosal administration.

In some embodiments, the veterinary subject is suffering from a wound or other injury to the skin and the veterinary decorin core protein is administered to inhibit scar formation. In some embodiments, the wound is the result of cosmetic or general surgery, injury to the skin, or injury causing proud flesh. In some embodiments, the scar is a keloid scar.

In some embodiments, the veterinary subject is suffering from an injury or disease to the eye. In some embodiments, the injury to the eye is the result of corneal surgery, an eye burn, an eye infection, and an abrasive injury.

In some embodiments, the veterinary subject is suffering from a lung disease. In some embodiments, the lung disease is selected from the group consisting of interstitial lung disease and pulmonary fibrosis. In some embodiments, the veterinary subject is suffering from kidney disease.

In some embodiments, the kidney disease is selected from the group consisting of diabetic nephropathy and renal fibrosis.

In some embodiments, the veterinary subject is suffering from liver disease. In some embodiments, the liver disease is selected from the group consisting of cirrhosis and hepatic fibrosis.

In some embodiments, the subject is suffering from a cancer. In some embodiments, cancer is an EGF Receptor or IGF-I receptor positive cancer.

In some embodiments, the veterinary subject is suffering from heart disease.

In some embodiments, the veterinary subject is suffering from a neurological trauma. In some embodiments, the neurological trauma is selected from a brain injury and a spinal cord injury.

DEFINITIONS

Figure 1:
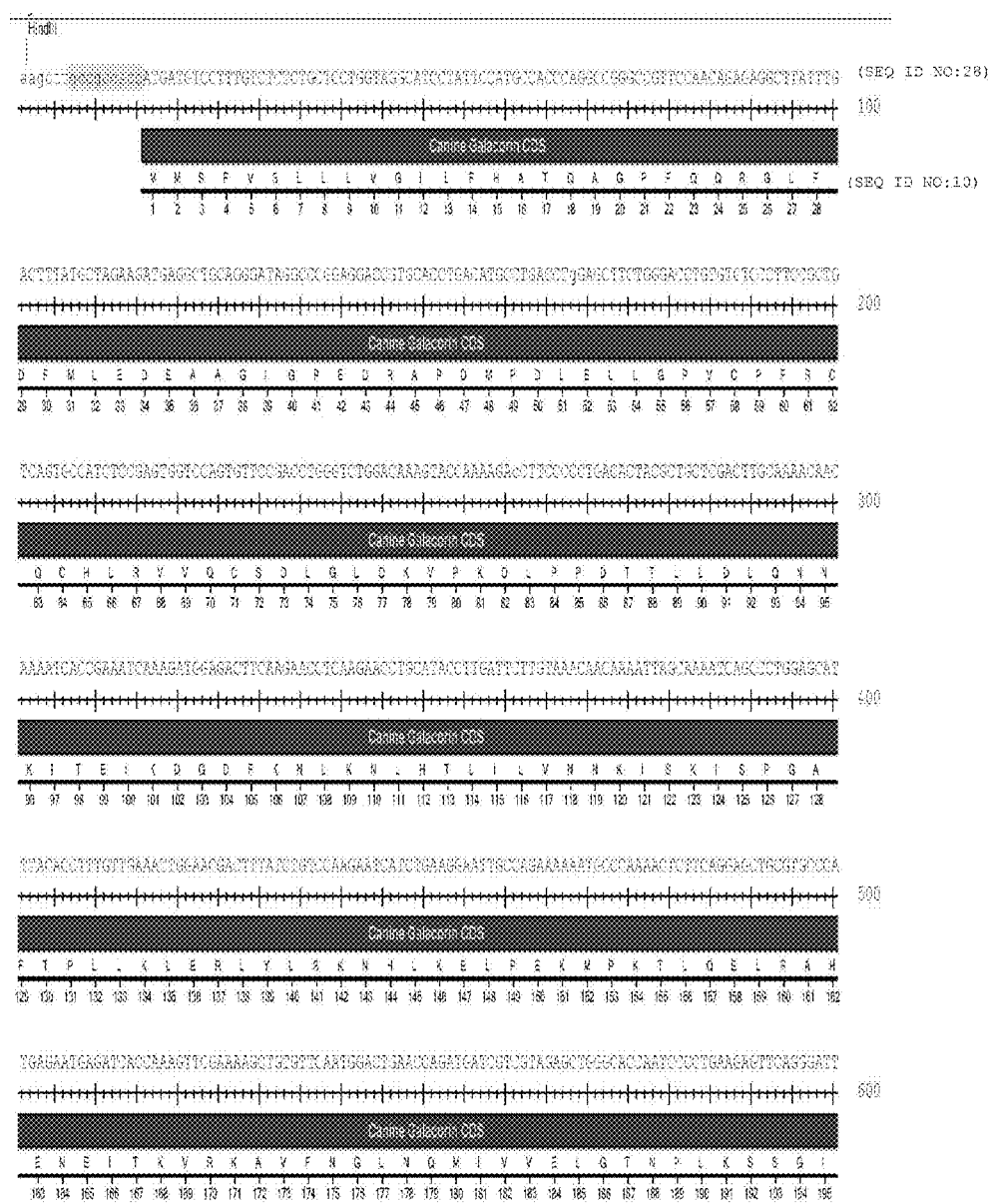
FIG. 1. Canine decorin coding sequence and the flanking DNA cloning junctions in the final retrovector expression construct are shown. Kozak translation initiation sequence is highlighted. The cloning sites HindIII and XhoI are also shown.
Figure 1:
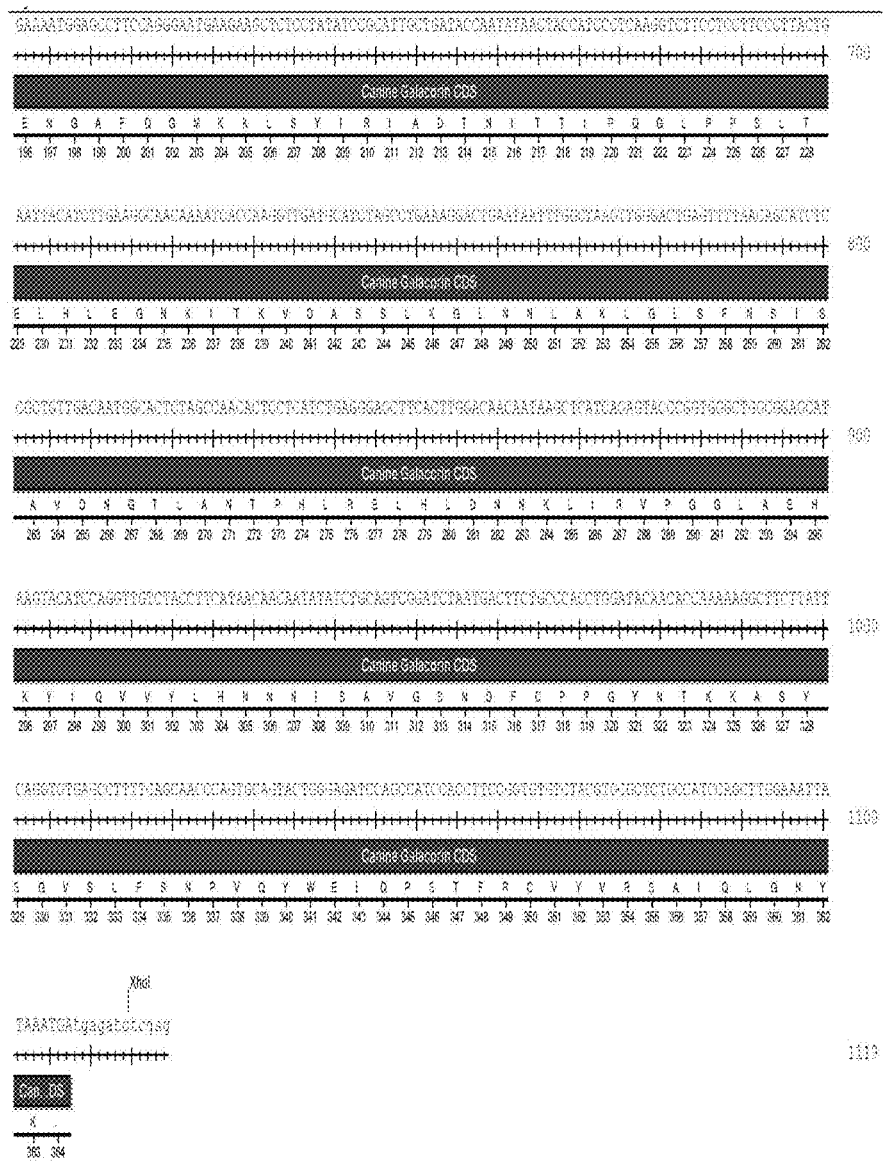
Figure 2:
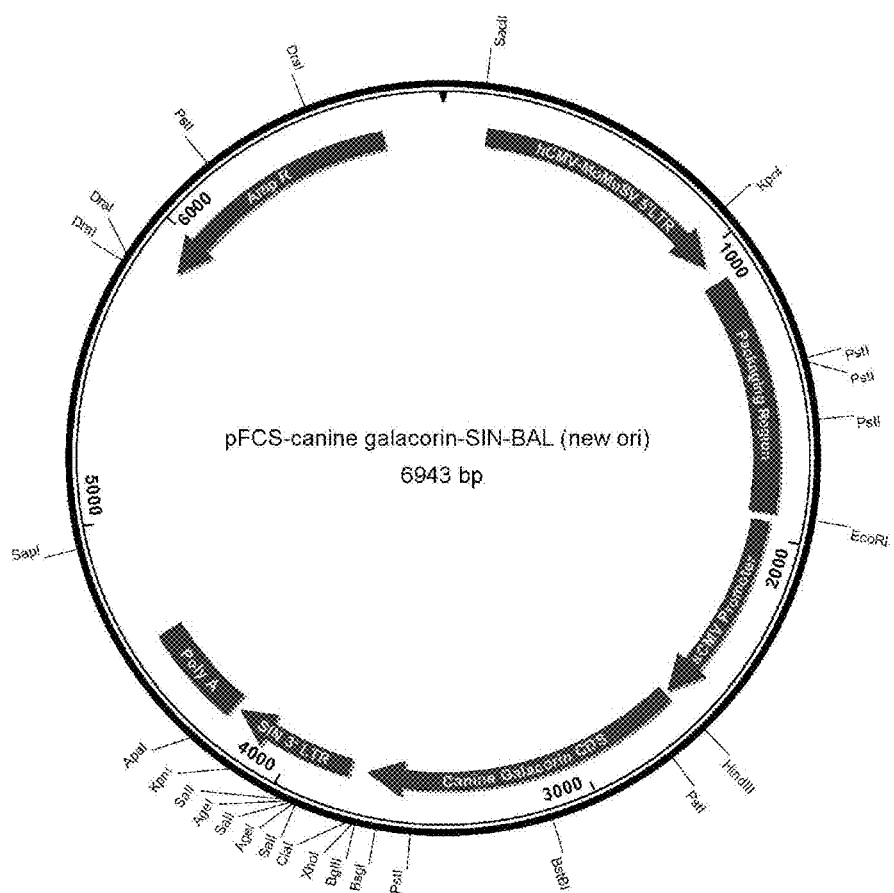
FIG. 2. Map of Canine Decorin in GPEX® Vector.
Figure 3:
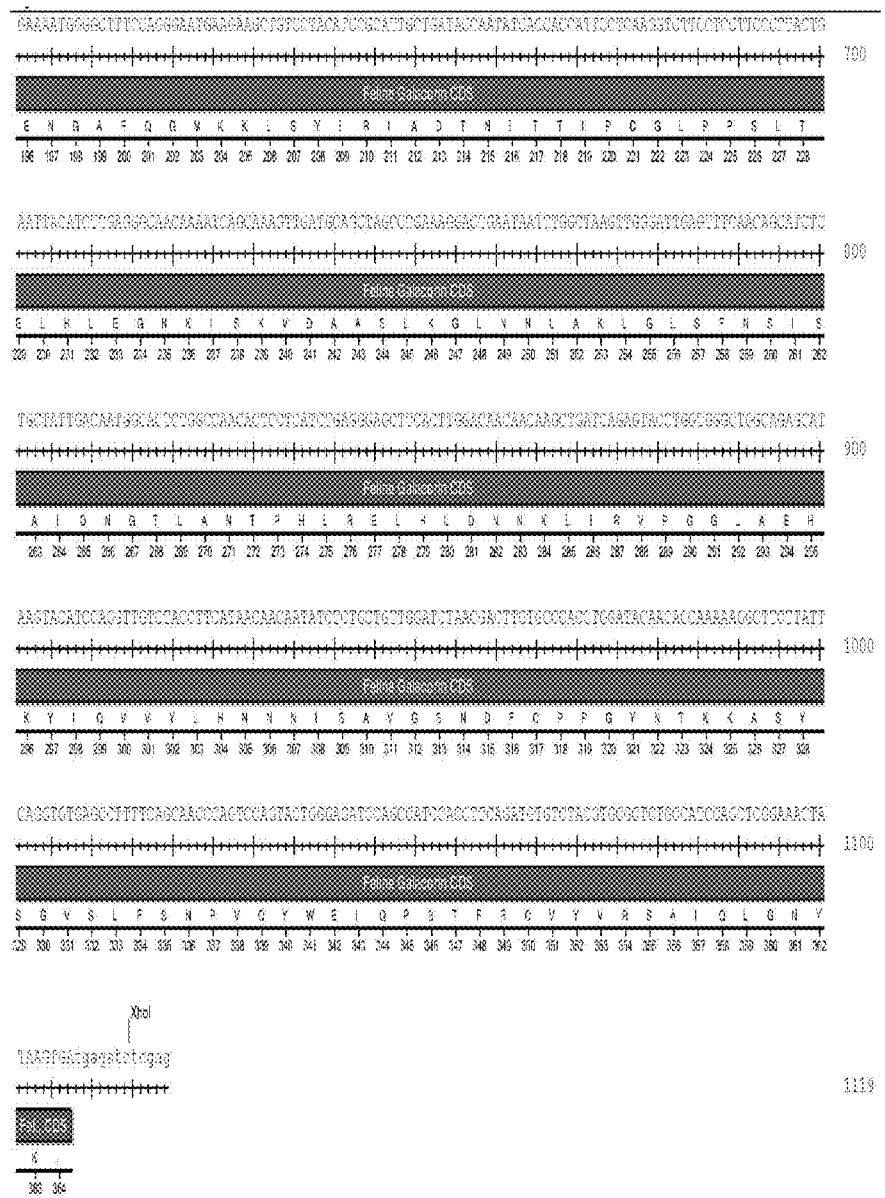
FIG. 3. Feline Decorin coding sequence and the flanking DNA cloning junctions in the final retrovector expression construct are shown. The Kozak translation initiation sequence is highlighted. The cloning sites HindIII and XhoI are also shown.
Figure 4:
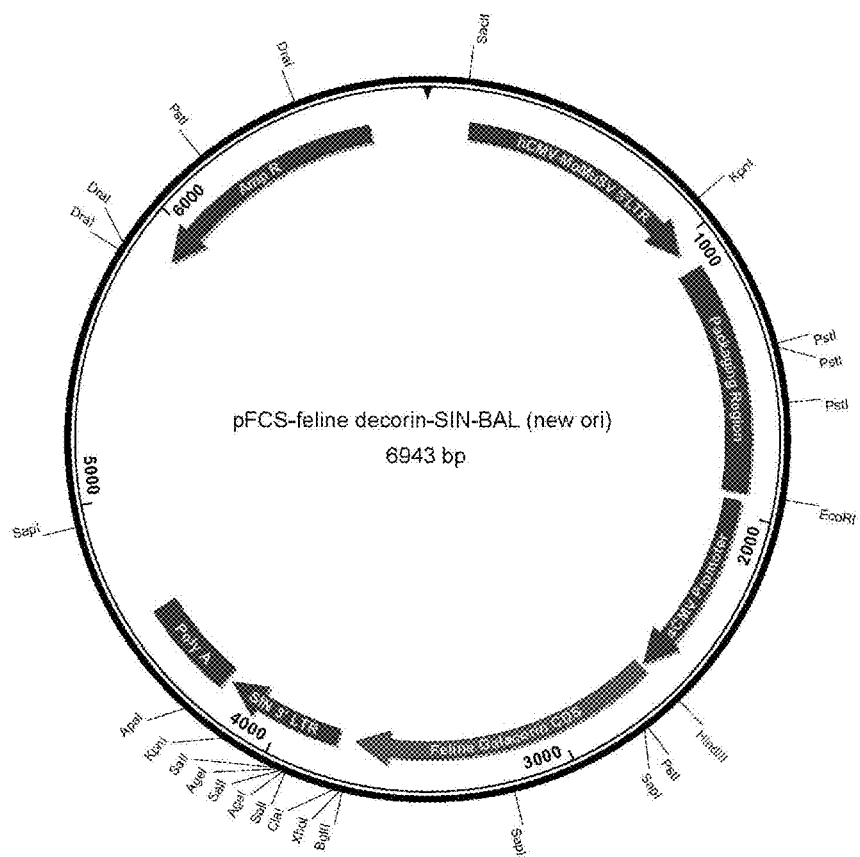
FIG. 4. Map of Feline Decorin in GPEX® Vector.

To facilitate understanding of the invention, a number of terms are defined below.

As used herein, the term "veterinary decorin" refers to a decorin molecule from a companion or stock animal, e.g., poultry such as a chicken, cows, goats, sheep, pigs, horses, dogs and cats.

As used herein, the term "veterinary decorin core protein" refers to a veterinary decorin protein molecule that has a mutation at amino acid 4 of mature decorin and that substantially lacks modification with a glycosaminoglycan (GAG; i.e., is non-gagylated) at amino acid 4.

As used herein, the term "veterinary subject" encompasses stock and companion animals, including, but not limited to, cows, sheep, horses, pigs, goats, chickens, turkeys, dogs and cats.

As used herein, the term "host cell" refers to any eukaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "homology" and "percent identity" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "signal sequence" refers to any DNA sequence which, when operably linked to a recombinant DNA sequence, encodes a signal peptide which is capable of causing the secretion of the recombinant polypeptide. In general, the signal peptides comprise a series of about 15 to 30 hydrophobic amino acid residues (See, e.g., Zwizinski et al., J. Biol. Chem. 255(16): 7973-77 [1980], Gray et al., Gene 39(2): 247-54 [1985], and Martial et al., Science 205: 602-607 [1979]). Such secretion signal sequences are preferably derived from genes encoding polypeptides secreted from the cell type targeted for tissue-specific expression (e.g., secreted milk proteins for expression in and secretion from mammary secretory cells). Secretory DNA sequences, however, are not limited to such sequences. Secretory DNA sequences from proteins secreted from many cell types and organisms may also be used (e.g., the secretion signals for t-PA, serum albumin, lactoferrin, and growth hormone, and secretion signals from microbial genes encoding secreted polypeptides such as from yeast, filamentous fungi, and bacteria).

As used herein, the term "purified" refers to molecules, either nucleic or amino acid sequences, that are removed from their normal environment, isolated or separated. An "isolated nucleic acid sequence" is therefore a purified nucleic acid sequence. "Substantially purified" molecules are at least 60% free, preferably at least 75% free, and more preferably at least 90% free from other components with which they are normally associated.

DETAILED DESCRIPTION OF THE INVENTION

The present invention relates to veterinary decorin compositions and methods of their production and use.

Decorin

Native decorin is a glycoprotein with an attached glycosaminoglycan and an average molecular weight of 90-140 kD. The present invention contemplates the production and use recombinant veterinary decorin. In some preferred embodiments, the veterinary decorin is a veterinary decorin core protein, i.e., a substantially non-gagylated veterinary decorin. In some embodiments, the veterinary decorin core protein comprises a mutation at amino acid 4 (i.e., the $4^{th}$ amino acid from the N-terminus) of the mature veterinary decorin core protein molecule. In some embodiments, the mutation is a serine to alanine mutation. In some embodiments, the veterinary decorin core protein molecule is a protein molecule having a sequence at least 90%, 95%, 96%, 97%, 98%, 99% or 100% identical to one of SEQ ID NOS:4 (chicken), 7 (bovine), 10 (canine), 13 (caprine), 16 (equine), 19 (porcine), 22 (ovine), and 27 (feline) provided that that the decorin core protein comprises a mutation at amino acid 4 (i.e., the $4^{th}$ amino acid from the N-terminus) of the mature decorin core protein molecule.

Decorin is commonly expressed as a pre-pro-protein. The present invention provides veterinary decorin fusion molecules comprising a heterologous signal sequence in operable association with the veterinary decorin pro-peptide and mature peptide sequences. In some embodiments, the heterologous signal polypeptide is an alpha-lactalbumin signal polypeptide. In some embodiments, the alpha-lactalbumin signal polypeptide is a bovine alpha-lactalbumin signal polypeptide. In some embodiments, the heterologous signal polypeptide is at least 80%, 90%, or 100% identical to MMSFVSLLLVGILFHATQA (SEQ ID NO:23). In some embodiments, the propeptide sequence is at least 80%, 90%, or 100% identical to the propeptide sequences identified in SEQ ID NOs:3, 6, 9, 12, 15, 18, 21 and 26. In some embodiments, the decorin core protein portion of the fusion polypeptide is at least 90%, 95%, 99% or 100% identical to SEQ ID NO:1 (mature decorin core protein), provided that that the decorin core protein comprises a mutation at amino acid 4 (i.e., the $4^{th}$ amino acid from the N-terminus) of the mature decorin core protein molecule. In some embodiments, the fusion protein is 90%, 95%, 96%, 97%, 98%, 99% or 100% identical to one of SEQ ID NOS:3 (chicken), 6 (bovine), 9 (canine), 12 (caprine), 15 (equine), 18 (porcine), 21 (ovine), and 26 (feline)(signal-propeptide veterinary decorin core protein), provided that that the decorin core protein comprises a mutation at amino acid 4 (i.e., the $4^{th}$ amino acid from the N-terminus) of the mature decorin core protein molecule.

The present invention further provides nucleic acid sequences encoding the fusion proteins, as well as vectors comprising the nucleic acid sequences. In some embodiments, the heterologous signal polypeptide is at least 80%, 90%, or 100% identical to ATGATGTCCTTTGTCTCTCT-GCTCCTGGTAGGCATCCTATTCCATGCCACCCAGGC C (SEQ ID NO:24). In some embodiments, the propeptide nucleic acid sequence is at least 80%, 90%, or 100% identical to the propeptide sequences identified in SEQ ID NOs:1, 5, 8, 11, 14, 17, 20 and 25. In some embodiments, the veterinary decorin core protein portion of the fusion polypeptide is at least 90%, 95%, 99% or 100% identical to the veterinary decorin core protein portion identified in SEQ ID NOs:1, 5, 8, 11, 14, 17, 20, and 25 provided that that the decorin core protein nucleic acid sequence comprises a mutation at amino acid 4 (i.e., the $4^{th}$ amino acid from the N-terminus) of the mature decorin core protein molecule. In some embodiments, the fusion protein is at least 90%, 95%, 99% or 100% identical to one of SEQ ID NOs: 1, 5, 8, 11, 14, 17, 20 and 25 (signal-propeptide veterinary decorin core protein nucleic acid sequences), provided that that the decorin core protein nucleic acid sequence comprises a mutation at amino acid 4 (i.e., the $4^{th}$ amino acid from the N-terminus) of the mature decorin core protein molecule.

The veterinary decorin polynucleotides of the present invention may be employed for producing veterinary decorin polypeptides by recombinant techniques. Thus, for example, the polynucleotide may be included in any one of a variety of expression vectors for expressing a polypeptide. In some embodiments of the present invention, vectors include, but are not limited to, retroviral vectors, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host. In some preferred embodiments, the vectors are retroviral vectors as described in U.S. Pat. Nos. 6,852,510 and 7,332,333 and U.S. Pat. Publ. Nos. 200402335173 and 20030224415, all of which are incorporated herein by references in their entirety. In some especially preferred embodiments, the vectors are pseudotyped retroviral vectors.

In particular, some embodiments of the present invention provide recombinant constructs comprising one or more of the sequences as broadly described above (e.g., one of SEQ ID NOs: 1, 5, 8, 11, 14, 17, 20 and 25). In some embodiments of the present invention, the constructs comprise a vector, such as a plasmid or viral vector, into which a sequence of the invention has been inserted, in a forward or reverse orientation. In still other embodiments, the heterologous structural sequence (e.g., one of SEQ ID NOs: 1, 5, 8, 11, 14, 17, 20 and 25) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial-pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic-pWLNEO, pSV2CAT, pOG44, PXT1, pSG (Stratagene) pSVK3, pBPV, pMSG, pSVL (Pharmacia); and 3) Baculovirus-pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin by 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, *Cell* 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by retroviral transduction, calcium phosphate transfection, DEAE-Dextran mediated transfection, or electroporation (See e.g., Davis et al. [1986] Basic Methods in Molecular Biology). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al. (1989) Molecular Cloning: A Laboratory Manual, Second Edition, Cold Spring Harbor, N.Y.

In some embodiments of the present invention, following transformation of a suitable host strain and growth of the host strain to an appropriate cell density in media, protein is secreted and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

The present invention also provides methods for recovering and purifying decorin from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In some embodiments, the present invention provides improved methods for the purification of decorin, especially decorin core protein. In some embodiments, the processes comprise two column chromatography steps and a polishing step.

In some preferred embodiments, cation exchange chromatography is used to capture decorin from medium containing decorin, preferably a clarified medium. In some embodiments, the cation exchange chromatography medium is SP-SEPHAROSE FF. In some embodiments, the cation exchange medium is equilibrated at about 5 to 15 mM sodium phosphate, preferably 10 mM sodium phosphate, and 20 to 70 mM NaCL, preferably about 50 mM NaCL at a neutral pH. In some embodiments, after application of the decorin containing medium to the cation exchange medium, the cation exchange medium is washed. In some embodiments, the wash buffer comprises about 5 to 15 mM sodium phosphate, preferably 10 mM sodium phosphate, and 20 to 70 mM NaCL, preferably about 50 mM NaCL. In some embodiments, decorin is then eluted from the cation exchange medium. In some embodiments, the elution buffer comprises about 5 to 15 mM sodium phosphate, preferably 10 mM sodium phosphate, and 150 to 250 mM NaCL, preferably about 200 mM NaCL.

In some embodiments, the eluate containing decorin from the cation exchange chromatography step is applied to a hydroxyapatite medium. In some embodiments, the hydroxyapatite medium is CHT Type 1. In some embodiments, the hydroxyapatite medium is equilibrated at about 5 to 15 mM sodium phosphate, preferably 10 mM sodium phosphate, and 150 to 250 mM NaCL, preferably about 200 mM NaCL. In some embodiments, after application of the decorin containing medium to the hydroxyapatite medium, the hydroxyapatite medium is washed. In some embodiments, the wash buffer comprises about 5 to 15 mM sodium phosphate, preferably 10 mM sodium phosphate, and 150 to 250 mM NaCL, preferably about 200 mM NaCL. In some embodiments, decorin is then eluted from the hydroxyapatite medium. In some embodiments, the elution buffer comprises about 0.2 to 0.4 M sodium phosphate, preferably 0.3 M sodium phosphate, and 150 to 250 mM NaCL, preferably about 200 mM NaCL.

In some embodiments, the eluate containing decorin from the hydroxyapatite chromatography step is buffer exchanged and applied to an ion exchange membrane. In some embodiments, the ion exchange membrane is a Q ion exchange membrane, for examples a MUSTANG Q ion exchange medium. In some embodiments, the membrane is equilibrated with from about 30 mM to 70 mM Tris-HCl, preferably about 50 mM Tris-HCl. In some embodiments, after application of the decorin-containing solution to the membrane, the membrane is washed and the decorin passes through the membrane. In some embodiments, the wash buffer comprises from about 30 mM to 70 mM Tris-HCl, preferably about 50 mM Tris-HCl. Following purification, the decorin is preferably concentrated to a desired concentration, for example by flow filtration.

In other embodiments of the present invention, solutions of containing the decorin are treated to inactivate or remove viruses. In some embodiments, solutions comprising decorin are treated with a surfactant to inactivate viruses. In some embodiments, the surfactant is TRITON X-100. In some embodiments, the surfactant treating step is performed after the cation exchange chromatography step. In some embodiments, the solutions comprising decorin are filtered to remove viruses. In some embodiments, the solutions are filtered through a viral Filter (e.g., a VIROSART viral filter). In some embodiments, the filtrations step is performed after the hydroxyapatite chromatography step.

The processes of the present invention preferably provide decorin compositions suitable for clinical use in human patients. In some embodiments, the compositions comprise a purified decorin core protein comprising a mutation at position 4 of the mature decorin core protein so that the decorin protein is substantially non-gagylated. In some embodiments, the compositions provide purified decorin proteins, and the compositions are characterized in comprising less than about 100, 50, 20, 10, 5 or 2 ng residual host cell protein/mg decorin core protein in the composition and/or less than about 20, 10, 5, or 2 pg residual host cell DNA/mg decorin core protein. In some embodiments, the decorin is provided in a aqueous solution. In some embodiments, the aqueous solution is phosphate buffered saline (e.g., 10 mM sodium phosphate, 150 mM sodium chloride), with a pH of from about 6.5 to 7.5, preferably about 7.0.

The present invention further provides pharmaceutical compositions comprising veterinary decorin purified as described above. Pharmaceutically acceptable carriers are well known in the art and include aqueous solutions such as physiologically buffered saline or other solvents or vehicles such as glycols, glycerol, vegetable oils (e.g., olive oil) or injectable organic esters. Further pharmaceutically acceptable carriers include, for example, hyaluronic acid, and aqueous solutions such as bicarbonate buffers, phosphate buffers, Ringer's solution and physiological saline supplemented with 5% dextrose or human serum albumin, if desired. A pharmaceutically acceptable carrier can be used to administer the decorin polypeptide to a cell in vitro or to a subject in vivo. A pharmaceutically acceptable carrier can contain a physiologically acceptable compound that acts, for example, to stabilize the polypeptide or to increase or decrease the absorption of the agent. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of a pharmaceutically acceptable carrier, including a physiologically acceptable compound, depends, for example, on the route of administration of the polypeptide and on the particular physio-chemical characteristics of the specific polypeptide. For example, a physiologically acceptable compound such as aluminum monosterate or gelatin is particularly useful as a delaying agent, which prolongs the rate of absorption of a pharmaceutical composition administered to a subject.

A pharmaceutical composition comprising an effective amount of veterinary decorin can be administered to a subject by various routes including, for example, topically, orally or parenterally, such as intravenously, intramuscularly, subcutaneously, intraperitoneally or by passive or facilitated absorption through the skin using, for example, a skin patch or transdermal iontophoresis, respectively. Topical administration can be passive, for example, by direct application of an ointment or powder, or active, for example, using a nasal spray or inhalant. Where the composition is administered as a topical spray, one component of the composition is an appropriate propellant. The pharmaceutical composition also can be incorporated, if desired, into liposomes, microspheres or other polymer matrices (Gregoriadis, Liposome Technology, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

An effective amount of the pharmaceutical composition comprising veterinary decorin is generally in the range of about 0.01 to 100 mg/kg body weight. An effective amount can be determined using methods known to those in the art. The total effective amount can be administered to a subject as a single dose, either as a bolus or by infusion over a relatively short period of time, or can be administered using a fractionated treatment protocol, in which the multiple doses are administered over a more prolonged period of time. One skilled in the art would know that the amount of decorin required to obtain an effective dose in a subject depends on many factors including the age and general health of the subject as well as the route of administration and the number of treatments to be administered. The veterinary decorin-containing compositions of the present invention can be combined with additional active agents. These agents include, but are not limited to, decorin-synthesis enhancers, collagen-synthesis enhancers, matrix metalloproteinases (MMP) inhibitors, antioxidants, collagen modulators, anti-wrinkle or anti-aging agents, antibiotics, depigmenting agents, analgesics, antimicrobials, anti-inflammatory agents, moisturizers, skin lightening agents, corticosteroids, or sun-block agents.

The veterinary decorin-containing compositions can be combined with a cosmetically or pharmaceutically or dermatologically acceptable carrier. The carriers include, but are not limited to, water, mineral oil, ethylene glycol, propylene glycol, lanolin, glyceryl stearate, sorbitan stearate, isopropyl myristate, isopropyl palmitate, acetone, glycerol, phosphatidylcholine, sodium cholate, or ethanol.

The veterinary decorin-containing compositions can be combined with a skin penetration enhancer. The enhancers, helping to transport the active components through the normal intact skin, include, but are not limited to, liposomes, mixed lipid micelles, ethosomes, transfersomes, niosomes, ethanol, amides, ethers, glycols, hydrocarbon oils, sodium lauryl sulfate, oleic acid, hydroalcoholic solution, and soya phosphatidylcholine or their combinations. Other skin penetration enhancement includes different pH values, co-solvents, surfactants, cyclodextrins, and iontophoresis.

A suitable carrier or vehicle or enhancer will include the formulation of gels, creams, lotions, solutions, colloidal dispersions, emulsions (oil-in-water or water-in-oil), foams, sprays, suspensions, sunscreens, liquid and various skin care preparations for topical application to the skin. The decorin-containing compositions can be prepared in any formula for topical application to the skin.

The formulation mentioned above can also be combined with other ingredients, depending on the intended use of the formulation. These ingredients include, but are not limited to, preservatives, vitamins, polymers, fragrances, water- or oil-soluble film formers, or flavoring agents.

The veterinary decorin compositions of the present invention find a variety of uses. While the methods utilizing veterinary decorin are generally applicable, specific examples of pathologies which can be treated include cancer, a fibrotic disease, and glomerulonephritis. In fibrotic cancer, for example, decorin can be used to bind TGF-β, destroying TGF-β's growth stimulating activity on the cancer cell. The veterinary decorin compositions further find use in treating tumors which are positive for the EGF receptor and/or IGF-1 receptor. Other proliferative pathologies include rheumatoid arthritis, arteriosclerosis, adult respiratory distress syndrome, cirrhosis of the liver, fibrosis of the lungs, kidneys, or liver, post-myocardial infarction, cardiac fibrosis, post-angioplasty restenosis, renal interstitial fibrosis and certain dermal fibrotic conditions such as keloids and dermal scarring. In some particularly preferred embodiments, the compositions are used to treat or inhibit scarring in the proud flesh of horses. In further embodiments, the compositions are used to treat injuries to the eye, for example, injury to the eye resulting from corneal surgery, eye burns (chemical or thermal), eye infections, and abrasive injuries to the eye. In some embodiments, the decorin compositions are used to treat heart disease. In still further embodiments, the decorin compositions are used to treat neurological traumas, such as brain or spinal cord injuries.

EXPERIMENTAL

Example 1

Expression constructs have been designed for a mutant form of veterinary decorin from a number of different species of companion animals and stock animals. A serine to alanine modification was made at amino acid 4 of mature decorin for each of the different species. The mutation prevents a GAG from being attached to the decorin molecule. The expression constructs use the bovine α-lactalbumin signal peptide instead of the endogenous signal peptide for protein production and secretion. The constructs are outlined below.

Chicken Decorin Expression Gene Sequence
(SEQ ID NO: 1):
ATGATGTCCTTTGTCTCTCTGCTCCTGGTAGGCATCCTATTCCAT

GCCACCCAGGCCGGACCATTTCAACAGAAAGGCTTATTTGACTTT

ATGCTGGAAGATGAGGCTGCAGGGATAGGCCCGGAAGAGCACTTT

CCTGAAGTTCCTGAAATAGAGCCTATGGGCCCAGTCTGCCCCTTC

CGCTGTCAGTGCCATCTGCGAGTTGTCCAGTGTTCTGATCTGGGT

CTGGAAAAAGTACCAAAAGACCTTCCTCCTGATACTGCGCTGCTG

GACCTGCAAAACAACAAAATAACTGAGATCAAAGATGGAGACTTT

AAGAACCTGAAGAACCTTCATACACTGATTCTCATCAACAACAAA

ATTAGCAAAATCAGCCCTGGGGCATTTGCTCCTTTGGTGAAATTG

GAACGACTTTATCTTTCCAAGAATCAACTGAAGGAATTGCCAGAG

AAAATGCCCAAAACTCTTCAGGAGCTGCGTGTCCATGAGAACGAG

ATCACCAAAGTGCGAAAGTCTGTGTTCAATGGATTGAACCAGATG

ATCGTCGTAGAACTTGGCACCAACCCGCTGAAGAGCTCAGGCATT

GAAAATGGAGCCTTTCAGGGAATGAAGAAGCTCTCCTACATCCGC

ATTGCTGACACAAATATAACTACCATCCCTCAAGGTCTTCCTCCT

TCCCTTACTGAATTACATCTCGATGGCAACAAAATCACCAAAGTT

GATGCAGCTAGCCTGAAAGGACTGAATAATTTGGCTAAGTTGGGA

CTGAGTTTCAACAGCATCTCTGCGGTTGACAATGGCTCTTTGGCC

AACACTCCTCATTTGAGGGAACTTCATTTGAACAACAACAAGCTT

GTCAAAGTGCCCGGTGGGCTGGCCGATCATAAGTACATCCAGGTT

GTCTACCTTCACAACAACAATATCTCTGCAATCGGCTCTAACGAC

TTCTGCCCACCCGGATACAACACCAAAAAGGCTTCTTATTCAGGA

GTGAGCCTTTTCAGCAACCCAGTCCAGTACTGGGAGATCCAGCCA

TCCACCTTCCGATGTGTCTATGTGCGTGCTGCCGTTCAGCTTGGA

AACTACAAGTGA

SEQ ID NO: 2:
ATGATGTCCTTTGTCTCTCTGCTCCTGGTAGGCATCCTATTCCAT

GCCACCCAGGCCACGCGGTTCCACCAGAAGGGCCTCTTTGACTTT

ATGATAGAGGATGAAGGGGCAGCCGACATGGCTCCAACAGATGAT

```
CCTGTCATATCTGGATTTGGGCCAGTGTGCCCCTTCCGCTGCCAG

TGTCATCTTCGCGTTGTGCAGTGCTCTGACCTAGGTCTGGAAAGA

GTGCCAAAAGACCTTCCCCCTGACACAACTCTGCTGGATTTACAG

AACAACAAAATCACTGAAATTAAAGAAGGAGATTTCAAGAATTTG

AAGAATCTTCATGCATTGATCCTTGTTAACAACAAAATCAGCAAA

ATAAGTCCGGCAGCTTTTGCTCCTCTGAAGAAACTGGAAAGACTG

TACCTATCCAAGAATAATTTGAAGGAACTTCCAGAAAACATGCCA

AAGTCTCTTCAGGAGATACGTGCTCATGAAAATGAGATCTCCAAG

TTGAGGAAGGCAGTTTTTAATGGACTGAATCAAGTGATTGTCTTA

GAACTAGGCACCAATCCACTCAAGAGCTCAGGCATTGAAAATGGA

GCTTTTCAAGGGATGAAGAGGCTTTCCTATATCCGCATCGCAGAC

ACCAACATTACTAGCATCCCTAAAGGTCTTCCTCCATCCCTTACT

GAGCTTCACCTTGATGGCAACAAAATTAGCAAAATTGATGCGGAA

GGTCTGTCTGGACTCACCAACTTGGCTAAATTGGGTCTCAGCTTC

AACAGTATTTCTTCTGTTGAAAATGGCTCTCTGAACAATGTACCT

CATCTGAGAGAACTTCATCTGAATAACAACGAACTTGTCAGAGTA

CCTAGTGGGTTGGGTGAACACAAATACATCCAGGTGGTCTATCTT

CATAACAACAAGATTGCTTCAATTGGTATCAACGACTTTTGCCCT

CTTGGCTACAACACCAAAAAGGCAACCTATTCTGGTGTGAGTCTC

TTCAGCAACCCCGTGCAGTACTGGGAAATCCAGCCCTCTGCTTTC

CGATGTATCCATGAACGCTCTGCAGTACAGATCGGAAATTACAAA

TGA
```

The bovine α-lactalbumin signal peptide coding region is shown in boldface type
The chicken decorin pro-peptide coding region is underlined
The mutated mature decorin coding region is shown in standard type

```
Chicken Decorin Expression Protein Sequence
(SEQ ID NO: 3):
MMSFVSLLLVGILFHATQATRFHQKGLFDFMIEDEGAADMAPTDD

PVISGFGPVCPFRCQCHLRVVQCSDLGLERVPKDLPPDTTLLDLQ

NNKITEIKEGDFKNLKNLHALILVNNKISKISPAAFAPLKKLERL

YLSKNNLKELPENMPKSLQEIRAHENEISKLRKAVFNGLNQVIVL

ELGTNPLKSSGIENGAFQGMKRLSYIRIADTNITSIPKGLPPSLT

ELHLDGNKISKIDAEGLSGLTNLAKLGLSFNSISSVENGSLNNVP

HLRELHLNNNELVRVPSGLGEHKYIQVVYLHNNKIASIGINDFCP

LGYNTKKATYSGVSLFSNPVQYWEIQPSAFRCIHERSAVQIGNYK.
```

The bovine α-lactalbumin signal peptide is shown in boldface type
The chicken decorin pro-peptide is underlined
  The mutated mature decorin coding region is shown in standard type (Amino acid #4 of mature decorin was mutated from a serine to an alanine to prevent addition of the GAG moiety to the mature protein. This amino acid is shown in boldface type as well as underlined).

```
Mature chicken decorin (SEQ ID NO: 4):
DEGAADMAPTDDPVISGFGPVCPFRCQCHLRVVQCSDLGLERVPKD

LPPDTTLLDLQNNKITEIKEGDFKNLKNLHALILVNNKISKISPAA

FAPLKKLERLYLSKNNLKELPENMPKSLQEIRAHENEISKLRKAVF

NGLNQVIVLELGTNPLKSSGIENGAFQGMKRLSYIRIADTNITSIP

KGLPPSLTELHLDGNKISKIDAEGLSGLTNLAKLGLSFNSISSVEN

GSLNNVPHLRELHLNNNELVRVPSGLGEHKYIQVVYLHNNKIASIG

INDFCPLGYNTKKATYSGVSLFSNPVQYWEIQPSAFRCIHERSAVQ

IGNYK

Cow Decorin Expression Gene Sequence (SEQ ID
NO: 5):
ATGATGTCCTTTGTCTCTCTGCTCCTGGTAGGCATCCTATTCCATG

CCACCCAGGCCGGACCATTTCAACAGAAAGGCTTATTTGACTTTAT

GCTGGAAGATGAGGCTGCAGGGATAGGCCCGGAAGAGCACTTTCCT

GAAGTTCCTGAAATAGAGCCTATGGGCCCAGTCTGCCCCTTCCGCT

GTCAGTGCCATCTGCGAGTTGTCCAGTGTTCTGATCTGGGTCTGGA

AAAAGTACCAAAAGACCTTCCTCCTGATACTGCGCTGCTGGACCTG

CAAAACAACAAAATAACTGAGATCAAAGATGGAGACTTTAAGAACC

TGAAGAACCTTCATACACTGATTCTCATCAACAACAAAATTAGCAA

AATCAGCCCTGGGGCATTTGCTCCTTTGGTGAAATTGGAACGACTT

TATCTTTCCAAGAATCAACTGAAGGAATTGCCAGAGAAAATGCCCA

AAACTCTTCAGGAGCTGCGTGTCCATGAGAACGAGATCACCAAAGT

GCGAAAGTCTGTGTTCAATGGATTGAACCAGATGATCGTCGTAGAA

CTTGGCACCAACCCGCTGAAGAGCTCAGGCATTGAAAATGGAGCCT

TTCAGGGAATGAAGAAGCTCTCCTACATCCGCATTGCTGACACAAA

TATAACTACCATCCCTCAAGGTCTTCCTCCTTCCCTTACTGAATTA

CATCTCGATGGCAACAAAATCACCAAAGTTGATGCAGCTAGCCTGA

AAGGACTGAATAATTTGGCTAAGTTGGGACTGAGTTTCAACAGCAT

CTCTGCGGTTGACAATGGCTCTTTGGCCAACACTCCTCATTTGAGG

GAACTTCATTTGAACAACAACAAGCTTGTCAAAGTGCCCGGTGGGC

TGGCCGATCATAAGTACATCCAGGTTGTCTACCTTCACAACAACAA

TATCTCTGCAATCGGCTCTAACGACTTCTGCCCACCCGGATACAAC

ACCAAAAAGGCTTCTTATTCAGGAGTGAGCCTTTTCAGCAACCCAG

TCCAGTACTGGGAGATCCAGCCATCCACCTTCCGATGTGTCTATGT

GCGTGCTGCCGTTCAGCTTGGAAACTACAAGTGA
```

The bovine α-lactalbumin signal peptide coding region is shown in boldface type
The bovine decorin pro-peptide coding region is underlined
The mutated mature decorin coding region is shown in standard type

```
Cow Decorin Expression Protein Sequence (SEQ
ID NO: 6):
MMSFVSLLLVGILFHATQAGPFQQKGLFDFMLEDEAAGIGPEEHFP

EVPEIEPMGPVCPFRCQCHLRVVQCSDLGLEKVPKDLPPDTALLDL
```

QNNKITEIKDGDFKNLKNLHTLILINNKISKISPGAFAPLVKLERL

YLSKNQLKELPEKMPKTLQELRVHENEITKVRKSVFNGLNQMIVVE

LGTNPLKSSGIENGAFQGMKKLSYIRIADTNITTIPQGLPPSLTEL

HLDGNKITKVDAASLKGLNNLAKLGLSFNSISAVDNGSLANTPHLR

ELHLNNNKLVKVPGGLADHKYIQVVYLHNNNISAIGSNDFCPPGYN

TKKASYSGVSLFSNPVQYWEIQPSTFRCVYVRAAVQLGNYK.

The bovine α-lactalbumin signal peptide is shown in boldface type
The bovine decorin pro-peptide is underlined
The mutated mature decorin coding region is shown in standard type (Amino acid #4 of mature decorin was mutated from a serine to an alanine to prevent addition of the GAG moiety to the mature protein. This amino acid is shown in boldface type as well as underlined)

```
Mature cow decorin protein sequence (SEQ
ID NO: 7):
DEAAGIGPEEHFPEVPEIEPMGPVCPFRCQCHLRVVQCSDLGLEKV

PKDLPPDTALLDLQNNKITEIKDGDFKNLKNLHTLILINNKISKIS

PGAFAPLVKLERLYLSKNQLKELPEKMPKTLQELRVHENEITKVRK

SVFNGLNQMIVVELGTNPLKSSGIENGAFQGMKKLSYIRIADTNIT

TIPQGLPPSLTELHLDGNKITKVDAASLKGLNNLAKLGLSFNSISA

VDNGSLANTPHLRELHLNNNKLVKVPGGLADHKYIQVVYLHNNNIS

AIGSNDFCPPGYNTKKASYSGVSLFSNPVQYWEIQPSTFRCVYVRA

AVQLGNYK

Dog Decorin Expression Gene Sequence (SEQ ID
NO: 8):
ATGATGTCCTTTGTCTCTCTGCTCCTGGTAGGCATCCTATTCCATG

CCACCCAGGCCGGGCCGTTCCAACAGAGAGGCTTATTTGACTTTAT

GCTAGAAGATGAGGCTGCAGGGATAGGCCCGGAGGACCGTGCACCT

GACATGCCTGACCTCGAGCTTCTGGGACCTGTGTGTCCCTTCCGCT

GTCAGTGCCATCTCCGAGTGGTCCAGTGTTCCGACCTGGGTCTGGA

CAAAGTACCAAAAGATCTTCCCCCTGACACTACGCTGCTCGACTTG

CAAAACAACAAAATCACCGAAATCAAAGATGGAGACTTCAAGAACC

TCAAGAACCTGCATACCTTGATTCTTGTAAACAACAAAATTAGCAA

AATCAGCCCTGGAGCATTTACACCTTTGTTGAAATTGGAACGACTT

TATCTGTCCAAGAATCATCTGAAGGAATTGCCAGAAAAAATGCCCA

AAACTCTTCAGGAGCTGCGTGCCCATGAGAATGAGATCACCAAAGT

TCGAAAAGCTGTGTTCAATGGACTGAACCAGATGATCGTCGTAGAG

CTGGGCACCAATCCCCTGAAGAGTTCAGGGATTGAAAATGGAGCCT

TCCAGGGAATGAAGAAGCTCTCCTATATCCGCATTGCTGATACCAA

TATAACTACCATCCCTCAAGGTCTTCCTCCTTCCCTTACTGAATTA

CATCTTGAAGGCAACAAAATCACCAAGGTTGATGCATCTAGCCTGA

AAGGACTGAATAATTTGGCTAAGTTGGGACTGAGTTTTAACAGCAT

CTCCGCTGTTGACAATGGCACTCTAGCCAACACTCCTCATCTGAGG
```

```
GAGCTTCACTTGGACAACAATAAGCTCATCAGAGTACCCGGTGGGC

TGGCGGAGCATAAGTACATCCAGGTTGTCTACCTTCATAACAACAA

TATATCTGCAGTCGGATCTAATGACTTCTGCCCACCTGGATACAAC

ACCAAAAAGGCTTCTTATTCAGGTGTGAGCCTTTTCAGCAACCCAG

TGCAGTACTGGGAGATCCAGCCATCCACCTTCCGGTGTGTCTACGT

GCGCTCTGCCATCCAGCTTGGAAATTATAAATGA
```

The bovine α-lactalbumin signal peptide coding region is shown in boldface type
The dog decorin pro-peptide coding region is underlined
The mutated mature decorin coding region is shown in standard type

```
Dog Decorin Expression Protein Sequence
(SEQ ID NO: 9):
MMSFVSLLLVGILFHATQAGPFQQRGLFDFMLEDEAAGIGPEDRAP

DMPDLELLGPVCPFRCQCHLRVVQCSDLGLDKVPKDLPPDTTLLDL

QNNKITEIKDGDFKNLKNLHTLILVNNKISKISPGAFTPLLKLERL

YLSKNHLKELPEKMPKTLQELRAHENEITKVRKAVENGLNQMIVVE

LGTNPLKSSGIENGAFQGMKKLSYIRIADTNITTIPQGLPPSLTEL

HLEGNKITKVDASSLKGLNNLAKLGLSFNSISAVDNGTLANTPHLR

ELHLDNNKLIRVPGGLAEHKYIQVVYLHNNNISAVGSNDFCPPGYN

TKKASYSGVSLFSNPVQYWEIQPSTFRCVYVRSAIQLGNYK.
```

The bovine α-lactalbumin signal peptide is shown in boldface type
The dog decorin pro-peptide is underlined
The mutated mature decorin coding region is shown in standard type (Amino acid #4 of mature decorin was mutated from a serine to an alanine to prevent addition of the GAG moiety to the mature protein. This amino acid is shown in boldface type as well as underlined)

```
Mature dog decorin sequence (SEQ ID NO: 10):
DEAAGIGPEDRAPDMPDLELLGPVCPFRCQCHLRVVQCSDLGLDKV

PKDLPPDTTLLDLQNNKITEIKDGDFKNLKNLHTLILVNNKISKIS

PGAFTPLLKLERLYLSKNHLKELPEKMPKTLQELRAHENEITKVRK

AVFNGLNQMIVVELGTNPLKSSGIENGAFQGMKKLSYIRIADTNIT

TIPQGLPPSLTELHLEGNKITKVDASSLKGLNNLAKLGLSFNSISA

VDNGTLANTPHLRELHLDNNKLIRVPGGLAEHKYIQVVYLHNNNIS

AVGSNDFCPPGYNTKKASYSGVSLFSNPVQYWEIQPSTFRCVYVRS

AIQLGNYK

Goat Decorin Expression Gene Sequence (SEQ ID
NO: 11):
ATGATGTCCTTTGTCTCTCTGCTCCTGGTAGGCATCCTATTCCATG

CCACCCAGGCCGGACCGTTTCAACAGAAAGGCTTATTTGACTTTAT

GCTGGAAGATGAGGCTGCAGGGATAGGCCCGGAAGAGCGCTTTCAT

GAAGTTCCTGAATTAGAGCCTATGGGCCCAGTCTGCCCCTTCCGCT

GTCAGTGCCATCTGCGAGTTGTCCAGTGTTCTGTTCTGGGTCTGGA

AAAAGTGCCCAAAGACCTTCCTCCTGATACCGCGCTGCTGGACCTG
```

-continued

```
CAAAACAACAAAATAACTGAGATCAAAGATGGAGACTTTAAGAACC
TGAAGAACCTTCATACACTGATTCTCATCAACAACAAAATTAGCAA
AATCAGCCCTGGGGCATTTGCTCCTCTGGTGAAATTGGAACGACTT
TATCTTTCCAAGAATCAACTGAAGGAATTGCCAGAGAAAATGCCCA
AAACTCTTCAGGAGCTGCGTGTCCATGAGAACGAGATCACCAAAGT
GCGAAAGTCTGTGTTCAATGGATTGAACCAGATGATCGTCGTAGAA
CTTGGCACCAACCCACTGAAGAGCTCAGGCATTGAAAATGGAGCCT
TTCAGGGAATGAAGAAGCTCTCCTACATCCGCATTGCTGACACTAA
TATAACTACCATTCCTCAAGGTCTTCCTCCTTCCCTTACTGAATTA
CATCTCGATGGCAACAAAATCACCAAAGTTGATGCAGCTAGCCTGA
AAGGACTGAATAATTTGGCTAAGTTGGGACTGAGTTTCAACAGCAT
CTCTGCTGTTGACAATGGCTCTTTAGCCAACACTCCTCATTTGAGG
GAACTTCATTTGAACAACAACAAGCTTGTCAAAGTGCCCGGTGGGC
TGGCCGACCATAAGTACATCCAGGTTGTCTACCTTCACAACAACAA
TATCTCTGCAATCGGCTCCAACGACTTCTGCCCACCCGGATACAAC
ACCAAAAAGGCTTCTTATTCAGGAGTGAGCCTTTTCAGCAACCCAG
TCCAGTACTGGGAGATCCAGCCATCCACCTTCCGATGTGTCTACGT
GCGCGCTGCTGTTCAGCTTGGAAACTACAAGTGA
```

The bovine α-lactalbumin signal peptide coding region is shown in boldface type
The goat decorin pro-peptide coding region is underlined
The mutated mature decorin coding region is shown in standard type

```
Goat Decorin Expression Protein Sequence (SEQ
ID NO: 12):
MMSFVSLLLVGILFHATQAGPFQQKGLFDFMLEDEAAGIGPEERFH
EVPELEPMGPVCPFRCQCHLRVVQCSVLGLEKVPKDLPPDTALLDL
QNNKITEIKDGDFKNLKNLHTLILINNKISKISPGAFAPLVKLERL
YLSKNQLKELPEKMPKTLQELRVHENEITKVRKSVFNGLNQMIVVE
LGTNPLKSSGIENGAFQGMKKLSYIRIADTNITTIPQGLPPSLTEL
HLDGNKITKVDAASLKGLNNLAKLGLSFNSISAVDNGSLANTPHLR
ELHLNNNKLVKVPGGLADHKYIQVVYLHNNNISAIGSNDFCPPGYN
TKKASYSGVSLFSNPVQYWEIQPSTFRCVYVRAAVQLGNYK.
```

The bovine α-lactalbumin signal peptide is shown in boldface type
The goat decorin pro-peptide is underlined
The mutated mature decorin coding region is shown in standard type (Amino acid #4 of mature decorin was mutated from a serine to an alanine to prevent addition of the GAG moiety to the mature protein. This amino acid is shown in boldface type as well as underlined)

```
Mature goat decorin protein sequence (SEQ ID
NO: 13):
DEAAGIGPEERFHEVPELEPMGPVCPFRCQCHLRVVQCSVLGLEKV
PKDLPPDTALLDLQNNKITEIKDGDFKNLKNLHTLILINNKISKIS
PGAFAPLVKLERLYLSKNQLKELPEKMPKTLQELRVHENEITKVRK
SVFNGLNQMIVVELGTNPLKSSGIENGAFQGMKKLSYIRIADTNIT
TIPQGLPPSLTELHLDGNKITKVDAASLKGLNNLAKLGLSFNSISA
VDNGSLANTPHLRELHLNNNKLVKVPGGLADHKYIQVVYLHNNNIS
AIGSNDFCPPGYNTKKASYSGVSLFSNPVQYWEIQPSTFRCVYVRA
AVQLGNYK Horse Decorin Expression Gene Sequence (SEQ
ID NO: 14):
ATGATGTCCTTTGTCTCTCTGCTCCTGGTAGGCATCCTATTCCATG
CCACCCAGGCCGGACCATTTCAACAGAGAGGCTTATTTGACTTCAT
GCTAGAAGATGAGGCTGCAGGGATTGGCCCAGAAGATCGCATTCAT
GAAGTTCTAGACTTAGAGCCTCTGGGACCAGTGTGTCCTTTCCGCT
GTCAGTGCCATCTTGAGTTGTCCAATGTTCTGATTTGGGTCTGGA
CAAAGTGCCCAAAGATCTTCCCCCTGACACCACGCTGCTGGACCTG
CAAAACAACAAAATAACCGAAATCAAAGATGGAGACTTTAAGAACC
TGAAGAATCTTCATGCGTTGATTCTTGTCAACAACAAAATTAGCAA
AATCAGCCCTGGAGCATTTACACCTTTGGTGAAACTGGAACGACTT
TATCTGTCCAAGAATCATTTGAAGGAATTGCCAGAAAAATGCCCA
AAACTCTTCAGGAGCTGCGTGTCCATGAGAACGAGATCACCAAAGT
GCGAAAAGCGGTGTTCAATGGACTGAACCAGATGATAGTCGTAGAA
CTGGGCACCAACCCACTGAAGAGCTCAGGAATTGAAAATGGAGCCT
TCCAGGGGATGAAGAAGCTGTCCTACATCCGCATTGCTGACACCAA
CATAACCACCATCCCTCCAGGTCTTCCTCCTTCCCTTACTGAATTA
CATCTTGATGGCAACAAAATCACCAAAGTTGATGCAGCTAGCCTGA
GAGGACTGAATAATTTGGCTAAATTGGGACTGAGTTTCAACAGCAT
CTCTGCTGTTGACAATGGCTCTCTGGCCAACACTCCTCATTTGAGG
GAACTTCACTTGGACAACAACAAGCTTATCAAAGTGCCTGGTGGGC
TGGCGGATCATAAGTACATCCAGGTTGTCTACCTTCATAACAACAA
TATCTCTGCAGTTGGATCTAATGACTTCTGCCCACCTGGATACAAC
ACCAAAAAGGCTTCTTATTCGGGTGTGAGCCTTTTCAGCAACCCAG
TCCAGTACTGGGAGATCCAGCCATCCACCTTCCGATGTGTCTATGT
GCGCTCTGCCATTCAGCTCGGAAACTACAAGTGA
```

The bovine α-lactalbumin signal peptide coding region is shown in boldface type
The horse decorin pro-peptide coding region is underlined
The mutated mature decorin coding region is shown in standard type

```
Horse Decorin Expression Protein Sequence
(SEQ ID NO: 15):
MMSFVSLLLVGILFHATQAGPFQQRGLFDFMLEDEAAGIGPEDRIH
EVLDLEPLGPVCPFRCQCHLRVVQCSDLGLDKVPKDLPPDTTLLDL
QNNKITEIKDGDFKNLKNLHALILVNNKISKISPGAFTPLVKLERL
YLSKNHLKELPEKMPKTLQELRVHENEITKVRKAVFNGLNQMIVVE
```

-continued
LGTNPLKSSGIENGAFQGMKKLSYIRIADTNITTIPPGLPPSLTEL

HLDGNKITKVDAASLRGLNNLAKLGLSFNSISAVDNGSLANTPHLR

ELHLDNNKLIKVPGGLADHKYIQVVYLHNNNISAVGSNDFCPPGYN

TKKASYSGVSLFSNPVQYWEIQPSTFRCVYVRSAIQLGNYK.

The bovine α-lactalbumin signal peptide is shown in bold-face type
The horse decorin pro-peptide is underlined
The mutated mature decorin coding region is shown in standard type (Amino acid #4 of mature decorin was mutated from a serine to an alanine to prevent addition of the GAG moiety to the mature protein. This amino acid is shown in boldface type as well as underlined)

Mature horse decorin protein sequence (SEQ ID NO: 16):
DEAAGIGPEDRIHEVLDLEPLGPVCPFRCQCHLRVVQCSDLGLDKV

PKDLPPDTTLLDLQNNKITEIKDGDFKNLKNLHALILVNNKISKIS

PGAFTPLVKLERLYLSKNHLKELPEKMPKTLQELRVHENEITKVRK

AVFNGLNQMIVVELGTNPLKSSGIENGAFQGMKKLSYIRIADTNIT

TIPPGLPPSLTELHLDGNKITKVDAASLRGLNNLAKLGLSFNSISA

VDNGSLANTPHLRELHLDNNKLIKVPGGLADHKYIQVVYLHNNNIS

AVGSNDFCPPGYNTKKASYSGVSLFSNPVQYWEIQPSTFRCVYVRS

AIQLGNYK

Pig Decorin Expression Gene Sequence (SEQ ID NO: 17):
ATGATGTCCTTTGTCTCTCTGCTCCTGGTAGGCATCCTATTCCATG

CCACCCAGGCCGGACCATTTCAACAGAAAGGCTTATTTGACTTTAT

GCTAGAAGATGAGGCTGCAGGGATAGGCCCAGAAGACCGCTTTCCT

GAAGTTCCTGAATTAGAGCCTCTGGGACCCATGTGTCCCTTCCGCT

GTCAATGCCATCTTCGAGTTGTCCAATGTTCTGATTTGGGTCTGGA

CAAAGTGCCCAAAGATCTTCCACCTGACACTGCCCTGCTGGATCTG

CAAAACAACAAAATAACTGAAATCAAAGATGGAGACTTTAAGAACC

TGAAGAACCTTCATACACTGATTCTCATCAACAACAAAATTAGCAA

AATCAGCCCTGGAGCATTTGCACCTTTGGTGAAATTGGAACGACTT

TATCTATCCAAGAATCAACTGAAGGAATTGCCAGAGAAAATGCCCA

AAACTCTTCAGGAGCTGCGTGTCCATGAGAATGAGATCACCAAAGT

GCGAAAGGCTGTGTTCAATGGATTGAACCAGATGATCGTCGTAGAA

CTTGGCACCAACCCGCTGAAGAGCTCAGGCATTGAAAACGGAGCTT

TCCAGGGAATGAAGAAGCTCTCCTACATCCGCATCGCTGACACCAA

CATTACCACCATCCCTCAAGGTCTTCCTCCTTCCCTTACTGAATTA

CATCTTGATGGCAACAAAATCAGCAAAGTTGATGCAGCTAGCCTAA

AAGGACTGAATAATTTGGCTAAGTTGGGACTGGGTTTCAATAGCAT

CTCAACTGTTGACAATGGCTCTCTGGCCAACACTCCTCATTTGAGG

GAACTTCATCTGAACAACAACAAGCTTAACAAAGTGCCTGGTGGGC

TGGCAGAGCATAAGTACATCCAGGTTGTCTACCTTCATAACAACAA

-continued
CATCTCTGCAGTCGGCTCTAATGACTTCTGCCCGCCTGGATACAAC

ACCAAAAAGGCTTCTTATTCGGGGGTGAGCCTTTTCAGCAACCCAG

TCCAGTACTGGGAGATCCAGCCATCCACCTTCCGATGTGTCTATGT

GCGCTCTGCCATTCAGCTCGGAAACTACAAGTGA

The bovine α-lactalbumin signal peptide coding region is shown in boldface type
The pig decorin pro-peptide coding region is underlined
The mutated mature decorin coding region is shown in standard type Pig Decorin Expression Protein Sequence (SEQ ID NO: 18):
MMSFVSLLLVGILFHATQAGPFQQKGLFDFMLEDEAAGIGPEDRFP

EVPELEPLGPMCPFRCQCHLRVVQCSDLGLDKVPKDLPPDTALLDL

QNNKITEIKDGDFKNLKNLHTLILINNKISKISPGAFAPLVKLERL

YLSKNQLKELPEKMPKTLQELRVHENEITKVRKAVFNGLNQMIVVE

LGTNPLKSSGIENGAFQGMKKLSYIRIADTNITTIPQGLPPSLTEL

HLDGNKISKVDAASLKGLNNLAKLGLGFNSISTVDNGSLANTPHLR

ELHLNNNKLNKVPGGLAEHKYIQVVYLHNNNISAVGSNDFCPPGYN

TKKASYSGVSLFSNPVQYWEIQPSTFRCVYVRSAIQLGNYK.

The bovine α-lactalbumin signal peptide is shown in boldface type
The pig decorin pro-peptide is underlined
The mutated mature decorin coding region is shown in standard type (Amino acid #4 of mature decorin was mutated from a serine to an alanine to prevent addition of the GAG moiety to the mature protein. This amino acid is shown in boldface type as well as underlined)

Mature pig decorin sequence (SEQ ID NO: 19):
DEAAGIGPEDRFPEVPELEPLGPMCPFRCQCHLRVVQCSDLGLDKV

PKDLPPDTALLDLQNNKITEIKDGDFKNLKNLHTLILINNKISKIS

PGAFAPLVKLERLYLSKNQLKELPEKMPKTLQELRVHENEITKVRK

AVFNGLNQMIVVELGTNPLKSSGIENGAFQGMKKLSYIRIADTNIT

TIPQGLPPSLTELHLDGNKISKVDAASLKGLNNLAKLGLGFNSIST

VDNGSLANTPHLRELHLNNNKLNKVPGGLAEHKYIQVVYLHNNNIS

AVGSNDFCPPGYNTKKASYSGVSLFSNPVQYWEIQPSTFRCVYVRS

AIQLGNYK

Sheep Decorin Expression Gene Sequence (SEQ ID NO: 20):
ATGATGTCCTTTGTCTCTCTGCTCCTGGTAGGCATCCTATTCCATG

CCACCCAGGCCGGACCGTTTCAACAGAAAGGCTTATTTGACTTTAT

GCTGGAAGATGAGGCTGCAGGGATAGGCCCGGAAGAGCGCTTTCAT

GAGGTTCCTGAATTAGAGCCTATGGGCCCAGTCTGCCCCTTCCGTT

GCCAGTGCCATCTGCGAGTTGTCCAGTGTTCTGATCTGGGTCTGGA

AAAAGTGCCCAAAGACCTTCCTCCTGATACCGCGCTGCTGGACCTG

CAAAACAACAAAATAACTGAGATCAAAGATGGAGACTTTAAAAACC

TGAAGAACCTTCATACACTGATTCTCATCAACAACAAAATTAGCAA

```
AATTAGCCCTGGGGCATTTGCTCCTCTGGTGAAATTGGAACGACTT

TATCTTTCCAAGAATCAACTGAAGGAATTGCCAGAGAAAATGCCCA

AAACTCTTCAGGAGCTGCGTGTCCATGAGAACGAGATCACCAAAGT

GCGAAAGTCTGTGTTCAATGGATTGAACCAGATGATCGTCGTAGAA

CTTGGCACCAACCCACTGAAGAGCTCAGGCATTGAAAATGGAGCCT

TTCAGGGAATGAAGAAGCTCTCCTACATCCGCATTGCTGACACTAA

TATAACTACCATCCCTCAAGGTCTTCCTCCTTCCCTTACTGAATTA

CATCTCGACGGCAACAAAATCACCAAAGTTGATGCAGCTAGCCTGA

AAGGACTGAATAATTTGGCTAAGTTGGGACTGAGTTTCAACAGCAT

CTCTGCTGTTGACAATGGCTCTTTGGCCAACACTCCTCATTTGAGG

GAACTTCATTTGAACAACAACAAGCTTGTCAAAGTGCCCGGTGGGC

TGGCCGACCATAAGTACATCCAGGTTGTCTACCTTCACAACAACAA

TATCTCTGCAATCGGCTCTAACGACTTCTGCCCACCTGGATACAAC

ACCAAAAAGGCTTCTTATTCAGGAGTGAGCCTTTTCAGCAACCCAG

TCCAGTACTGGGAGATCCAGCCATCCACCTTCCGATGTGTCTACGT

GCGCGCTGCTGTTCAGCTTGGAAACTACAAGTGA
```

The bovine α-lactalbumin signal peptide coding region is shown in boldface type
The sheep decorin pro-peptide coding region is underlined
The mutated mature decorin coding region is shown in standard type

```
Sheep Decorin Expression Protein Sequence
(SEQ ID NO: 21):
MMSFVSLLLVGILFHATQAGPFQQKGLFDFMLEDEAAGIGPEERFH

EVPELEPMGPVCPFRCQCHLRVVQCSDLGLEKVPKDLPPDTALLDL

QNNKITEIKDGDFKNLKNLHTLILINNKISKISPGAFAPLVKLERL

YLSKNQLKELPEKMPKTLQELRVHENEITKVRKSVFNGLNQMIVVE

LGTNPLKSSGIENGAFQGMKKLSYIRIADTNITTIPQGLPPSLTEL

HLDGNKITKVDAASLKGLNNLAKLGLSFNSISAVDNGSLANTPHLR

ELHLNNNKLVKVPGGLADHKYIQVVYLHNNNISAIGSNDFCPPGYN

TKKASYSGVSLFSNPVQYWEIQPSTFRCVYVRAAVQLGNYK.
```

The bovine α-lactalbumin signal peptide is shown in boldface type
The sheep decorin pro-peptide is underlined
The mutated mature decorin coding region is shown in standard type (Amino acid #4 of mature decorin was mutated from a serine to an alanine to prevent addition of the GAG moiety to the mature protein. This amino acid is shown in boldface type as well as underlined)

```
Mature sheep decorin protein sequence (SEQ
ID NO: 22):
DEAAGIGPEERFHEVPELEPMGPVCPFRCQCHLRVVQCSDLGLEKV

PKDLPPDTALLDLQNNKITEIKDGDFKNLKNLHTLILINNKISKIS

PGAFAPLVKLERLYLSKNQLKELPEKMPKTLQELRVHENEITKVRK

SVFNGLNQMIVVELGTNPLKSSGIENGAFQGMKKLSYIRIADTNIT
```

```
TIPQGLPPSLTELHLDGNKITKVDAASLKGLNNLAKLGLSFNSISA

VDNGSLANTPHLRELHLNNNKLVKVPGGLADHKYIQVVYLHNNNIS

AIGSNDFCPPGYNTKKASYSGVSLFSNPVQYWEIQPSTFRCVYVRA

AVQLGNYK

Feline Decorin Expression Gene Sequence
(SEQ ID NO: 25)
ATGATGTCCTTTGTCTCTCTGCTCCTGGTAGGCATCCTATTCCATG

CCACCCAGGCCGGGCCGTTCCAACAGAGAGGCTTATTTGACTTTAT

GCTAGAAGATGAGGCTGCAGGGATAGGCCCAGAAGAGCACGCTCCT

GTTGATTCTGATTTAGAGCCTCTGGGGCCAGTGTGTCCTTTCCGCT

GTCAGTGCCACCTTCGAGTTGTGCAGTGTTCTGATTTGGGTTTGGA

AAAAGTGCCAAAAGAGCTCCCTCCTGACACTACGCTGCTGGACTTG

CAAAACAACAAAATAACCGAAATCAAAGATGGAGACTTCAAGAACC

TGAAGAACCTTCATACGTTGATCCTTGTCAACAACAAAATTAGCAA

AATCAGCCCTGGAGCATTTACACCTTTGTTGAAATTGGAACGACTT

TATCTGTCCAAGAATCATCTGAAGGAATTGCCAGAAAAATGCCCA

AAACTCTTCAGGAGCTGCGTGCTCACGAGAATGAGATCACCAAAGT

GCGAAAAGCTGTGTTCAATGGCCTGAACCAGATGATCGTCGTAGAA

CTGGGCACCAACCCGCTGAAGAGCTCGGGAATTGAAAATGGAGCCT

TCCAGGGAATGAAGAAGCTGTCCTACATCCGCATTGCCGACACCAA

TATAACCACCATCCCGCAAGGTCTTCCTCCTTCCCTTACTGAATTA

CATCTTGAAGGCAACAAAATCTCCAAAGTTGATGCAGCTAGCCTGA

AAGGACTGAATAATTTGGCTAAGTTGGGACTGAGTTTTAACAGCAT

CTCTGCTATTGACAATGGCACTCTGGCCAACACTCCTCATTTGAGG

GAGCTTCACTTGGACAACAATAAGCTTATCAGAGTACCTGGTGGGC

TGGCGGAGCACAAATACATCCAGGTTGTCTACCTTCATAACAACAA

TATCTCTGCAGTCGGGTCTAACGACTTCTGCCCACCTGGATACAAC

ACCAAAAAGGCTTCTTATTCAGGTGTGAGCCTTTTCAGCAACCCAG

TCCAGTACTGGGAGATCCAACCATCCACCTTCCGATGTGTCTATGT

GCGTTCCGCCATCCAGCTTGGAAATTATAAATGA
```

The bovine α-lactalbumin signal peptide coding region is shown in boldface type
The cat decorin pro-peptide coding region is underlined
The mutated mature decorin coding region is shown in standard type

```
Feline Decorin Expression Protein Sequence
(SEQ ID NO: 26)
MMSFVSLLLVGILFHATQAGPFQQRGLFDFMLEDEAAGIGPEEHAP

VDSDLEPLGPVCPFRCQCHLRVVQCSDLGLEKVPKELPPDTTLLDL

QNNKITEIKDGDFKNLKNLHTLILVNNKISKISPGAFTPLLKLERL

YLSKNHLKELPEKMPKTLQELRAHENEITKVRKAVENGLNQMIVVE

LGTNPLKSSGIENGAFQGMKKLSYIRIADTNITTIPQGLPPSLTEL

HLEGNKISKVDAASLKGLNNLAKLGLSFNSISAIDNGTLANTPHLR
```

-continued

```
ELHLDNNKLIRVPGGLAEHKYIQVVYLHNNNISAVGSNDFCPPGYN

TKKASYSGVSLFSNPVQYWEIQPSTFRCVYVRSAIQLGNYK
```

The bovine α-lactalbumin signal peptide is shown in boldface type

The cat decorin pro-peptide is underlined

The mutated mature decorin coding region is shown in standard type (Amino acid #4 of mature decorin was mutated from a serine to an alanine to prevent addition of the GAG moiety to the mature protein. This amino acid is shown in boldface type as well as underlined)

```
Mature feline decorin protein sequence (SEQ
ID NO: 27):
DEAAGIGPEEHAPVDSDLEPLGPVCPFRCQCHLRVVQCSDLGLEKV

PKELPPDTTLLDLQNNKITEIKDGDFKNLKNLHTLILVNNKISKIS

PGAFTPLLKLERLYLSKNHLKELPEKMPKTLQELRAHENEITKVRK

AVFNGLNQMIVVELGTNPLKSSGIENGAFQGMKKLSYIRIADTNIT

TIPQGLPPSLTELHLEGNKISKVDAASLKGLNNLAKLGLSFNSISA

IDNGTLANTPHLRELHLDNNKLIRVPGGLAEHKYIQVVYLHNNNIS

AVGSNDFCPPGYNTKKASYSGVSLFSNPVQYWEIQPSTFRCVYVRS

AIQLGNYK
```

Example 2

Gene Construct Development

Canine and Feline Decorin DNA construction and cloning. The Canine and Feline gene sequences of decorin were synthesized with the bovine alpha-lactalbumin signal peptide attached. Both DNA sequences were cloned into Catalent's GPEX® expression vectors (FIGS. 1-4). See, e.g., Bleck, G. T. 2005 An alternative method for the rapid generation of stable, high-expressing mammalian cell lines (A Technical Review). Bioprocessing J. September/October pp 1-7; Bleck, G. T., 2010. GPEX® A Flexible Method for the Rapid Generation of Stable, High Expressing, Antibody Producing Mammalian Cell Lines Chapter 4 In: Current Trends in Monoclonal Antibody Development and Manufacturing, Biotechnology: Pharmaceutical Aspects, Edited by: S. J. Shire et al. © 2010 American Association of Pharmaceutical Scientists, DOI 10.1007/978-0-387-76643-0_4.

CHO Cell Line Development

Retrovector Production.

The expression constructs outlined above were introduced into a HEK 293 cell line that constitutively produces the MLV gag, pro, and pol proteins. An envelope containing expression plasmid was also co-transfected with the decorin gene construct. The co-transfection resulted in the production of replication incompetent high titer retrovector that was concentrated by ultracentrifugation and used for cell transductions (1,2).

Transduction of GCHO Cells with Retrovector.

The Canine and Feline Decorin pooled cell lines were made by performing multiple rounds of transduction of the GPEX® Chinese Hamster Ovary (GCHO) parental cell line with retrovector made from the gene constructs developed to express the two decorin molecules. Three independent transductions were performed to generate a pooled cell line for each of the two products.

Fed Batch Production of Canine and Feline from the Pooled Population of Cells.

Figure 5:
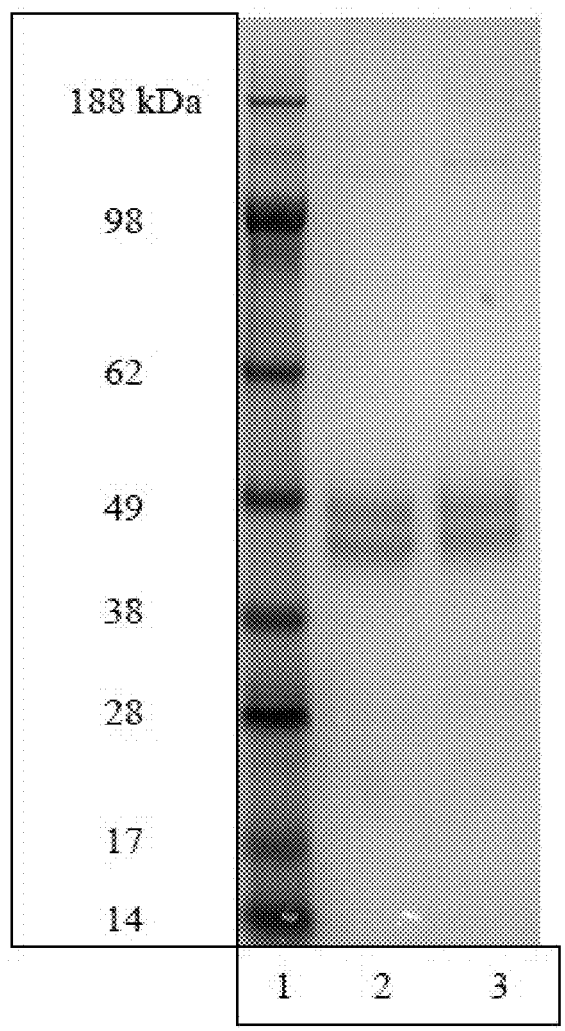
FIG. 5. SDS-PAGE gel of media from the pooled CHO cell line expressing Canine decorin mature protein. Lane 1. Molecular weight standards. Lane 2. Non-reduced media sample. Lane 3. Reduced media sample. The decorin protein shows as a doublet in both conditions similar to the purified human decorin shown in FIG. 7.
Figure 6:
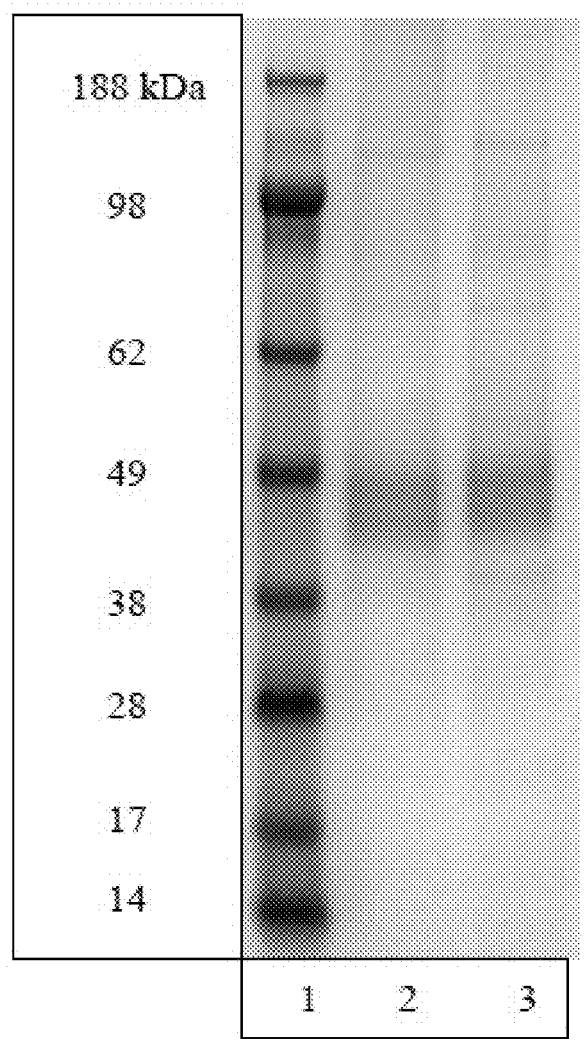
FIG. 6. SDS-PAGE gel of media from the pooled CHO cell line expressing Feline decorin mature protein. Lane 1. Molecular weight standards. Lane 2. Non-reduced media sample. Lane 3. Reduced media sample. The decorin protein shows as a doublet in both conditions similar to the purified human decorin shown in FIG. 7.
Figure 7:
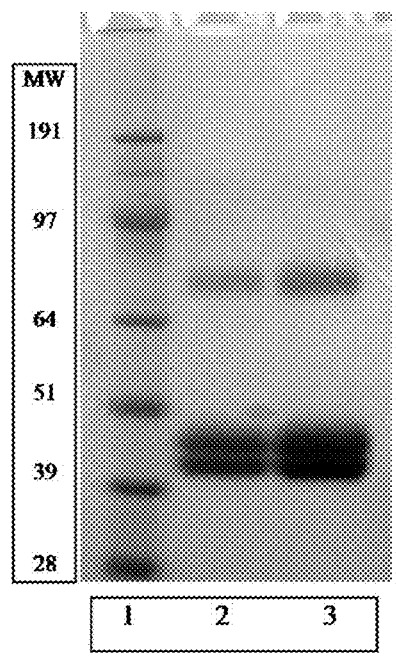
FIG. 7. SDS-PAGE gel of purified human decorin mature protein. Lane 1. Molecular weight standards. Lane 2. 2 mg human decorin (reduced). Lane 3. 5 mg human decorin (reduced).

Post-transduction, the pooled cell lines for Canine and Feline decorin were scaled up for productivity in a fed batch study in duplicate 250 mL shake flasks. Each shake flask was seeded with 300,000 viable cells per mL in a 60 mL working volume of PF-CHO LS media (HYCLONE) and incubated in a humidified (70-80%) shaking incubator at 130 rpm with 5% CO2 and temperature of 37° C. Cultures were fed four times during the production run using two different feed supplements. Cultures were terminated when viabilities were ≤50% (Day 14). Confirmation of canine and feline decorin production was determined by SDS-PAGE gel analysis (FIGS. 5 and 6). The traditional doublet associated with the human form (see FIG. 7) of this molecule was observed for both canine and feline.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of this invention are intended to be within the scope of the following claims.

What is claimed is:

1. A veterinary decorin core protein molecule that is at least 98% identical to one of SEQ ID NOs:4, 7, 10, 13, 16, 19, 22, and 27, wherein the veterinary core protein molecule comprises an aspartic acid residue at the N-terminus and does not comprise a serine residue at the fourth amino acid from the N-terminus.

2. The veterinary decorin core protein molecule of claim 1, wherein said protein molecule is at least 99% identical to one of SEQ ID NOs:4, 7, 10, 13, 16, 19, 22, and 27, wherein the veterinary core protein molecule comprises an aspartic acid residue at the N-terminus and does not comprise a serine residue at the fourth amino acid from the N-terminus.

3. The veterinary decorin core protein molecule of claim 1, wherein said protein molecule is 100% identical to one of SEQ ID NOs:4, 7, 10, 13, 16, 19, 22, and 27.

4. The veterinary decorin core protein molecule of claim 1, wherein said core molecule is operably linked to a signal peptide that is exogenous to said veterinary decorin core protein molecule.

5. The veterinary decorin core protein molecule of claim 4, wherein said signal peptide is a bovine lactalbumin signal peptide.

6. A composition comprising a veterinary decorin core protein molecule according to claim 1 in combination with a pharmaceutically acceptable carrier.

* * * * *